(12) United States Patent
Sciavolino et al.

(10) Patent No.: US 9,999,626 B2
(45) Date of Patent: *Jun. 19, 2018

(54) MINERAL AMINO-ACID COMPLEXES OF ACTIVE AGENTS

(71) Applicant: Thetis Pharmaceuticals LLC, Southport, CT (US)

(72) Inventors: Frank C. Sciavolino, Waterford, CT (US); Gary Mathias, Ridgefield, CT (US)

(73) Assignee: Thetis Pharmaceuticals LLC, Branford, CT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/772,035

(22) PCT Filed: Jun. 12, 2015

(86) PCT No.: PCT/US2015/035686
§ 371 (c)(1),
(2) Date: Sep. 1, 2015

(87) PCT Pub. No.: WO2015/195491
PCT Pub. Date: Dec. 23, 2015

(65) Prior Publication Data
US 2016/0199385 A1 Jul. 14, 2016

Related U.S. Application Data

(60) Provisional application No. 62/058,491, filed on Oct. 1, 2014, provisional application No. 62/013,904, filed on Jun. 18, 2014.

(51) Int. Cl.

| | | |
|---|---|---|
| *A61K 31/555* | (2006.01) | |
| *A23L 1/29* | (2006.01) | |
| *A61K 31/20* | (2006.01) | |
| *A61K 31/201* | (2006.01) | |
| *A61K 31/202* | (2006.01) | |
| *C07F 1/00* | (2006.01) | |
| *A23L 5/00* | (2016.01) | |
| *A61K 31/7135* | (2006.01) | |
| *C07F 3/02* | (2006.01) | |
| *C07F 3/04* | (2006.01) | |
| *C07F 3/06* | (2006.01) | |
| *A61K 45/06* | (2006.01) | |
| *A23L 29/00* | (2016.01) | |
| *A23L 33/10* | (2016.01) | |
| *A23L 33/16* | (2016.01) | |
| *A23L 33/175* | (2016.01) | |
| *A23L 33/18* | (2016.01) | |

(52) U.S. Cl.
CPC ............ *A61K 31/555* (2013.01); *A23L 1/296* (2013.01); *A23L 5/00* (2016.08); *A23L 29/015* (2016.08); *A23L 33/10* (2016.08); *A23L 33/16* (2016.08); *A23L 33/175* (2016.08); *A23L 33/18* (2016.08); *A61K 31/20* (2013.01); *A61K 31/201* (2013.01); *A61K 31/202* (2013.01); *A61K 31/7135* (2013.01); *A61K 45/06* (2013.01); *C07F 1/005* (2013.01); *C07F 3/02* (2013.01); *C07F 3/04* (2013.01); *C07F 3/06* (2013.01); *A23V 2002/00* (2013.01)

(58) Field of Classification Search
CPC .. A61K 31/7135; A61K 31/20; A61K 31/201; A61K 31/202; A61K 31/555; A61K 45/06; C07F 1/005; C07F 3/02; C07F 3/04; C07F 3/06; A23V 2250/06–2250/0654; A23V 2250/1882; A23V 2250/1578; A23V 2250/161; A23V 2250/1642
USPC ......................................... 514/492, 494, 558
See application file for complete search history.

(56) References Cited

U.S. PATENT DOCUMENTS

| | | |
|---|---|---|
| 4,599,152 A | 7/1986 | Ashmead |
| 4,863,898 A * | 9/1989 | Ashmead ............. A61K 31/195 514/15.4 |
| 5,795,909 A | 8/1998 | Shashoua et al. |
| 6,372,790 B1 | 4/2002 | Bonhomme et al. |
| 6,491,950 B1 | 12/2002 | Gutierrez-Rocca et al. |
| 6,517,870 B1 | 2/2003 | Nishii et al. |
| 6,602,902 B2 | 8/2003 | Shashoua et al. |
| 6,667,064 B2 | 12/2003 | Surette |
| 6,720,001 B2 | 4/2004 | Chen et al. |
| 6,881,854 B2 | 4/2005 | Ptock et al. |
| 6,893,627 B2 | 5/2005 | Ribnicky et al. |
| 7,105,572 B2 | 9/2006 | Sato |
| 7,195,914 B2 | 3/2007 | Surette |
| 7,199,151 B2 | 4/2007 | Shashoua et al. |
| 7,214,387 B2 | 5/2007 | Sanghvi et al. |
| 7,223,770 B2 | 5/2007 | Zhang et al. |
| 7,304,089 B2 | 12/2007 | Kramer et al. |

(Continued)

FOREIGN PATENT DOCUMENTS

| | | |
|---|---|---|
| AU | 2012227298 A1 | 4/2014 |
| CN | 103340300 A | 10/2013 |

(Continued)

OTHER PUBLICATIONS

Scifinder search result of substances in US 2012/0258087 A1 (accessed on Mar. 1, 2017).*

(Continued)

*Primary Examiner* — My-Chau T. Tran
(74) *Attorney, Agent, or Firm* — Mintz Levin Cohn Ferris Glovsky and Popeo, P.C.; Muriel Liberto, Esq.

(57) ABSTRACT

The present invention provides compounds of Formula I and related compositions and methods.

57 Claims, 4 Drawing Sheets

(56) References Cited

U.S. PATENT DOCUMENTS

| | | | |
|---|---|---|---|
| 7,429,395 B2 | 9/2008 | Campbell-Tofte | |
| 7,553,870 B2 | 6/2009 | Shibuya | |
| 7,579,025 B2 | 8/2009 | Campbell-Tofte | |
| 7,619,002 B2 | 11/2009 | Shibuya | |
| 7,666,898 B2 | 2/2010 | Chang et al. | |
| 7,670,612 B2 | 3/2010 | Miller | |
| 7,973,073 B2 | 7/2011 | Mylari et al. | |
| 8,034,842 B2 | 10/2011 | Bryhn et al. | |
| 8,058,312 B2 | 11/2011 | Kim et al. | |
| 8,076,377 B2 | 12/2011 | Kim et al. | |
| 8,178,707 B2 | 5/2012 | Gleason et al. | |
| 8,378,131 B2 | 2/2013 | Gleason et al. | |
| 8,642,073 B2 * | 2/2014 | Mannino | A61K 9/1274 424/450 |
| 8,710,041 B2 | 4/2014 | Osterloh et al. | |
| 8,765,811 B2 | 7/2014 | Mylari et al. | |
| 8,906,964 B2 | 12/2014 | Bobotas et al. | |
| 8,933,124 B2 | 1/2015 | Mylari et al. | |
| 9,012,501 B2 | 4/2015 | Sachetto et al. | |
| 9,242,008 B2 | 1/2016 | Sciavolino et al. | |
| 9,505,709 B2 * | 11/2016 | Mathias | C07K 5/06095 |
| 2003/0077335 A1 | 4/2003 | Richardson et al. | |
| 2003/0220301 A1 | 11/2003 | Lal et al. | |
| 2005/0158374 A1 | 7/2005 | Wong et al. | |
| 2005/0165102 A1 | 7/2005 | Wong et al. | |
| 2005/0182029 A1 | 8/2005 | Lal | |
| 2005/0182089 A1 | 8/2005 | Friedl et al. | |
| 2006/0159746 A1 | 7/2006 | Troup et al. | |
| 2006/0229359 A1 | 10/2006 | Zhang et al. | |
| 2006/0240095 A1 | 10/2006 | Junien et al. | |
| 2007/0060532 A1 | 3/2007 | Junien et al. | |
| 2007/0092461 A1 | 4/2007 | Gupta | |
| 2007/0207196 A1 | 9/2007 | Zhang | |
| 2008/0045559 A1 | 2/2008 | Zhang et al. | |
| 2008/0200533 A1 | 8/2008 | Krishnan | |
| 2008/0260819 A1 | 10/2008 | Fleming et al. | |
| 2009/0047340 A1 | 2/2009 | Guilford | |
| 2009/0054513 A1 | 2/2009 | Webster et al. | |
| 2009/0156612 A1 | 6/2009 | Kuroita et al. | |
| 2009/0227560 A1 | 9/2009 | Kuroita et al. | |
| 2010/0035990 A1 | 2/2010 | Bryhn et al. | |
| 2010/0105773 A1 | 4/2010 | Smith et al. | |
| 2010/0121048 A1 | 5/2010 | Kuroita et al. | |
| 2010/0137587 A1 | 6/2010 | Takanobu et al. | |
| 2010/0324010 A1 | 12/2010 | Imaeda et al. | |
| 2011/0046053 A1 | 2/2011 | Kidron | |
| 2011/0052678 A1 | 3/2011 | Shantha et al. | |
| 2011/0171142 A1 | 7/2011 | Lara | |
| 2011/0237813 A1 | 9/2011 | Gleason et al. | |
| 2012/0178813 A1 | 7/2012 | Mylari et al. | |
| 2012/0189569 A1 | 7/2012 | Gupta | |
| 2012/0258087 A1 * | 10/2012 | Jedlinski | A23L 2/39 424/94.1 |
| 2013/0095140 A1 | 4/2013 | Baron et al. | |
| 2013/0281535 A1 | 10/2013 | Mylari et al. | |
| 2013/0281536 A1 | 10/2013 | Pinchera et al. | |
| 2014/0100273 A1 | 4/2014 | Bobotas et al. | |
| 2014/0107360 A1 | 4/2014 | Mylari et al. | |
| 2014/0118419 A1 | 5/2014 | Wu et al. | |
| 2014/0249221 A1 | 9/2014 | Mylari et al. | |

FOREIGN PATENT DOCUMENTS

| | | |
|---|---|---|
| EP | 2705844 A1 | 3/2014 |
| JP | 2004-175790 A | 6/2004 |
| WO | WO-03068209 | 8/2003 |
| WO | WO-03/093449 A2 | 11/2003 |
| WO | WO-03/093449 A3 | 11/2003 |
| WO | WO-2004/028469 A2 | 4/2004 |
| WO | WO-2004082402 A2 | 9/2004 |
| WO | WO-2005041923 A1 | 5/2005 |
| WO | WO-2005042539 A1 | 5/2005 |
| WO | WO-2005118612 A1 | 12/2005 |
| WO | WO-2009038396 A2 | 3/2009 |
| WO | WO-2010/12799 A2 | 2/2010 |
| WO | WO-2010127099 A2 | 11/2010 |
| WO | WO-2013103902 A1 | 7/2013 |
| WO | WO-2014/011814 A1 | 1/2014 |
| WO | WO-2014/011895 A2 | 1/2014 |
| WO | WO-2014/011895 A3 | 1/2014 |

OTHER PUBLICATIONS

MacLean et al., "Systematic review of the effects of n3 fatty acids in inflammatory bowel disease", 2005, Am. J. Clin. Nutr., 82(3), pp. 611-619. (Year: 2005).*

Farrukh et al., "Is there a role for fish oil in inflammatory bowel disease?", World J. Clin. Cases, Jul. 16, 2014, 2(7), pp. 250-252. (Year: 2014).*

Piazzi et al., "Eicosapentaenoic acid free fatty acid prevents and suppresses colonic neoplasia in colitis-associated colorectal cancer acting on Notch signaling and gut microbiota", Nov. 2014, Int. J. Cancer, 135(9), pp. 2004-2013. (Year:2014).*

"Amino Acid Structures." Web. Nov. 14, 2013. http://www.cem.msu.edu/-cem252/sp97/ch24/ch24aa/html.

"Cold Spring Harbor Protocols." 2006. Web. Nov. 13, 2013. http://cshprotocols.cship.org.

"Eicosapentaenoic Acid pKa." STN Registry File. Web. Nov. 14, 2013.

"Prandimet." RxList. Web. Nov. 14, 2013. http://www.rxlist.com/prandimet-drug.htm.

Charles et al. "Treatment with Metformin of Non-Diabetic Men with Hypertension, Hypertriglyceridaemia and Central Fat Distribution: The BIGPRO 1.2 Trial." *Diabetes Metab. Res. Rev.* 16(2000):2-7.

Goldberg et al. "Lifestyle and Metformin Treatment Favorably Influence Lipoprotein Subfraction Distribution in the Diabetes Prevention Program." *J. Clin. Endocrinol. Metab.* pub. ahead of print Aug. 26, 2013.

Sugiyama et al. "Eicosapentaenoic Acid Lowers Plasma and Liver Cholesterol Levels in the Presence of Peroxisome Profferators-Activate Receptor Alpha." *Life Sciences.* 83(2008):19-28.

Wulffele et al. "The Effect of Metformin on Blood Pressure, Plasma Cholesterol and Triglycerides in Type 2 Diabetes Mellitus: A Systematic Review." *J. Intern. Med.* 256.1(2004):1-14.

International Search Report issued in PCT/US2013/049984 dated Nov. 28, 2013.

Alagha, A. et al. (2011). "The preparation and crystal structure of acetatobis(L-arginine)zinc(II) acetate trihydrate, the first reported x-ray structure of a zinc(II)-arginine complex," *Inorganica Chimica Acta* 377(1):185-187.

Hartwell. I.O. et al. (Mar. 1970). "Preparation and Characterization of Tyrosine and Lysine Metal Chelate Polyesters and Polyamides," *Journal of the American Chemical Society* 92(5):1284-1289.

International Search Report dated Sep. 16, 2015, for PCT Application No. PCT/US2015/035686, filed Jun. 12, 2015, 6 pages.

Written Opinion dated Sep. 16, 2015, for PCT Application No. PCT/US2015/035686, filed Jun. 12, 2015, 13 pages.

* cited by examiner

Mineral Amino Acid Complex
of Fatty Acids

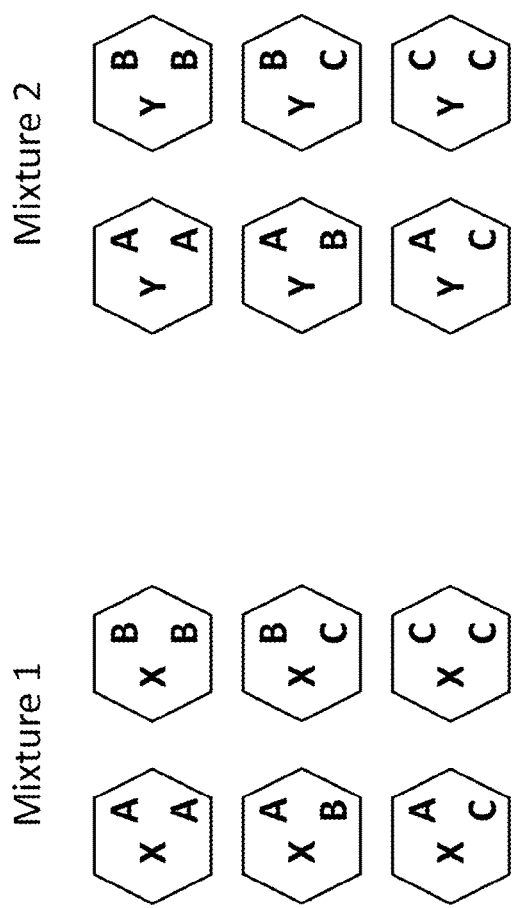

MINERAL AMINO-ACID COMPLEXES OF ACTIVE AGENTS

RELATED APPLICATION

This application is a national stage application, filed under 35 U.S.C. § 371, of International Application No. PCT/US2015/35686 filed Jun. 12, 2015, which claims priority to U.S. Provisional Application Nos. 62/058,491 filed Oct. 1, 2014 and 62/013,904 filed on Jun. 18, 2014, the contents of which are hereby incorporated by reference in their entireties.

FIELD OF THE INVENTION

The present invention relates to the field of drug delivery and particularly the use of mineral amino acid comprising salts of active agents and related compositions to deliver the active agents to a subject.

BACKGROUND

Amino acid chelates for delivery of minerals to biological tissues are described in U.S. Pat. No. 4,863,898 and U.S. Pat. No. 4,599,152 (Albion). Amino acid chelates in this context refers to the product resulting from the reaction of a polypeptide, dipeptide or naturally occurring alpha amino acid with a metal ion having a valence of two or more to form a ring structure in which the positive electrical charges of the metal ion are neutralized by the electrons available through the carboxylate or free amino groups of the alpha amino acid. As described by U.S. Pat. No. 4,863,898, chelate formation through neutralization of the positive charges of the divalent metal ions can be through the formation of ionic, covalent or coordinate covalent bonding. U.S. Pat. No. 4,863,898 states that it provides an advantage over the prior art metal chelates, which are effective to increase metal content in biological tissues generally, by providing metal chelates targeted to specific tissues. Manganese, calcium, iron, magnesium, copper, and zinc amino acid chelates are among those described.

Polyunsaturated fatty acids of the omega-3 series ("omega-3 fatty acids") have shown a wide spectrum of biological activities suggesting their possible usefulness in treating a range of diseases and disorders including metabolic disorders, cardiovascular complications, inflammatory diseases, central nervous system disorders, and ophthalmic complications. There are three major types of omega-3 fatty acids involved in the human physiology: α-linolenic acid (ALA; found in plant oils), eicosapentaenoic acid (EPA), and docosahexaenoic acid (DHA) (both commonly found in marine oils). Marine algae and phytoplankton are also sources of omega-3 fatty acids. Common sources of plant oils containing the omega-3 ALA fatty acid include walnut, edible seeds, clary sage seed oil, algal oil, flaxseed oil, Sacha Inchi oil, Echium oil, and hemp oil, while sources of animal omega-3 EPA and DHA fatty acids include fish oils, egg oil, squid oils, and krill oil. Often these primary omega-3 fatty acids are present with numerous minor omega-3 fatty acids as mixtures. But the poor aqueous solubility of omega-3 fatty acids limits their utility as therapeutic agents and as nutraceutical additives to food and drink due to a phenomenon referred to as solubility-limited absorption which limits the plasma levels that can be achieved following oral administration. In fact, the omega-3 fatty acids are essentially insoluble in water and both the free acid and sodium salt forms create soap-like emulsions when mixed with water. Thus, although omega-3 fatty acids are absorbed following oral administration, the relatively low plasma levels achieved cannot be increased simply by increasing the dose administered.

In addition to their poor aqueous solubility, omega-3 fatty acids suffer from susceptibility to lipid oxidation. This oxidation leads to formation of undesirable fishy and rancid off-flavors that render compositions comprising them less palatable.

WO 2014011895 describes fatty acid salts of eicosapentaenoic acid (EPA) with lysine or docosahexaenoic acid (DHA) or EPA with metformin, piperazine, and meglumine.

US 2011237813 (Jost Chemical Co.) describes mineral co-salts of polyunsaturated fatty acids and a non-fatty acid co-anion formed as a precipitate.

WO 2004082402 (Novartis AG) describes a combination, such as a combined preparation or pharmaceutical or nutritional composition, respectively, which comprises at least one cis-polyunsaturated fatty acid, at least one amino acid, and optionally at least one diabetes medicine for simultaneous, separate or sequential use in the prevention, delay of progression or treatment of diseases, especially metabolic disorders and in particular type 2 diabetes.

There is a need to develop new compositions able to deliver omega-3 fatty acids at much higher plasma levels than is possible using the currently available free fatty acid, sodium salt, or ester forms, in order to fulfill the therapeutic and nutritional promise of these compounds and translate the many promising in vitro and cellular pharmacology observations into clinical and general health benefits. The present invention addresses these needs.

SUMMARY OF THE INVENTION

The invention provides compounds of Formula I, including enantiomers, polymorphs, solvates, and hydrates thereof:

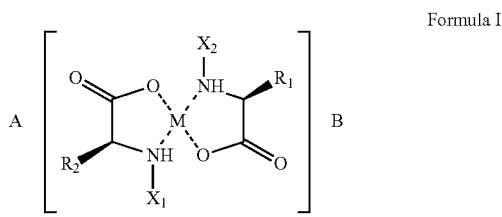

Formula I wherein $R_1$ and $R_2$ each refer to a branched or unbranched carbon chain of from 1 to 20 carbons having at least one basic function;

$R_1$ and $R_2$ are the same or different;

$X_1$ and $X_2$ are independently selected from H and —CO—Z, where Z is a peptide moiety incorporating from 1 to 5 amino acids, or a pharmaceutically acceptable salt thereof;

$X_1$ and $X_2$ are the same or different;

M is a divalent metal cation selected from magnesium ($Mg^{2+}$), calcium ($Ca^{2+}$), and zinc ($Zn^{2+}$);

A and B are each a molecule having at least one acid function, either A or B, but not both, may be absent, and when both A and B are present, A and B may be the same or different.

In one embodiment, the basic function of $R_1$ and $R_2$ is selected from a primary amine, a secondary amine, a tertiary amine, and a guanidine. In one embodiment, $R_1$ and $R_2$ are independently selected from $(CH_2)_3$—$Y_1$, and $(CH_2)_4$—$Y_2$, where $Y_1$ and $Y_2$ are each a basic function which may be the same or different. In one embodiment, $X_1$ and $X_2$ are each H. In one embodiment, $R_1$ and $R_2$ are each $(CH_2)_3$—$Y_1$ and $Y_1$ is $NHC(NH_2+)NH_2$. In one embodiment, $R_1$ and $R_2$ are each $(CH_2)_4$—$Y_2$ and $Y_2$ is $NH_3+$. In one embodiment, $R_1$ is $(CH_2)_4$—$Y_2$, $Y_2$ is $NH_3+$, $R_2$ is $(CH_2)_3$—$Y_1$, and $Y_1$ is $NHC(NH_2+)NH_2$.

In one embodiment, A or B, or both, is a fatty acid. In one embodiment, the invention provides a composition comprising one or more Formula I compounds in which A or B, or both, is a fatty acid. In one embodiment, the composition comprises a mixture of two or more different Formula I compounds in which A or B, or both, is a fatty acid. In one embodiment, the invention provides a composition comprising one or more Formula I compounds in which each of A and B is a fatty acid. In one embodiment, the composition comprises a mixture of two or more different Formula I compounds in which each of A and B is a fatty acid. In accordance with any of the foregoing embodiments, each fatty acid may be independently selected from a naturally occurring, non-naturally occurring, branched or unbranched mono-, di- or poly-unsaturated fatty acid having from about 8 carbon atoms to about 20 carbon atoms. In one embodiment, the fatty acid is independently selected from an omega-3 fatty acid, an omega-6 fatty acid, an omega-7 fatty acid, and an omega-9 fatty acid. In one aspect of this embodiment, A and B are each independently selected from eicosapentaenoic acid (EPA), docosahexaenoic acid (DHA), and docosapentaenoic acid (DPA), hexadecatrienoic acid (HTA), α-Linolenic acid (ALA), stearidonic acid (SDA), eicosenoic acid, eicosatrienoic acid (ETE), all-cis-5,8,11-eicosatrienoic acid, eicosatetraenoic acid (ETA), heneicosapentaenoic acid (HPA), tetracosapentaenoic acid, tetracosahexaenoic acid, linoleic acid, gamma-linolenic acid (GLA), calendic acid, eicosadienoic acid, dihomo-gamma-linolenic acid (DGLA), arachidonic acid, adrenic acid, docosadienoic acid, docosapentaenoic acid (Osbond acid), tetracosapentaenoic acid, 24:5 (n-6), tetracosatetraenoic acid, palmitoleic acid, vaccenic acid, paullinic acid, oleic acid, elaidic acid, gondoic acid, mead acid, erucic acid, and nervonic acid. In a further aspect, the polyunsaturated fatty acid is an omega-3 fatty acid selected from the group consisting of eicosapentaenoic acid (EPA), docosahexaenoic acid (DHA), docosapentaenoic acid (DPA), hexadecatrienoic acid (HTA), α-linolenic acid (ALA), stearidonic acid (SDA), eicosatrienoic acid (ETE), eicosatetraenoic acid (ETA), heneicosapentaenoic acid (HPA), tetracosapentaenoic acid, and tetracosahexaenoic acid. In a particular embodiment, the omega-3 fatty acid is selected from eicosapentaenoic acid (EPA), docosahexaenoic acid (DHA), and docosapentaenoic acid (DPA). In one embodiment, the polyunsaturated fatty acid is an omega-6 fatty acid selected from the group consisting of linoleic acid, gamma-linolenic acid (GLA), eicosadienoic acid, dihomo-gamma-linolenic acid (DGLA), arachidonic acid, docosadienoic acid, adrenic acid, docosapentaenoic acid (Osbond acid), tetracosatetraenoic acid, and tetracosapentaenoic acid, 24:5 (n-6). In one embodiment, the polyunsaturated fatty acid is an omega-9 fatty acid selected from the group consisting of mead acid, 20:3 (n-9), all-cis-5,8, 11-eicosatrienoic acid, oleic acid, eicosenoic acid, erucic acid, and nervonic acid. In one embodiment, where the composition comprises a mixture of two or more Formula I compounds in which A or B, or both, is a fatty acid, the mixture comprises at least 3, at least 4, at least 5, at least 6, at least 7, or at least 8 different compounds; or wherein the mixture comprises from 2 to 4, from 2 to 8, from 2 to 12, from 2 to 15 or from 2 to 20 different compounds. In one embodiment, the mixture is a mixture of two or more Formula I compounds in which A and B are each a fatty acid.

In one embodiment, the invention provides a compound selected from the group consisting of Calcium L-lysinate bis-EPA monohydrate, Calcium L-lysinate mono-EPA, Calcium L-lysinate bis-DHA, Magnesium L-lysinate bis-EPA dihydrate, Magnesium L-lysinate mono-EPA, Magnesium L-lysinate bis-DHA dihydrate, Magnesium L-lysinate mono-EPA mono-DHA dihydrate, Magnesium L-lysinate bis-stearic acid, Magnesium L-lysinate bis-linoleic acid, Magnesium L-lysinate bis-oleic acid, Magnesium L-lysinate bis-palmitic acid, Magnesium L-lysinate bis-linolenic acid, Magnesium L-lysinate bis docosapentaenoic acid, Zinc L-lysinate bis-EPA monohydrate, an enantiomer, polymorph, solvate, or hydrate of any of the foregoing, mixtures comprising two or more of the foregoing, and compositions comprising one, two or more of the foregoing.

In one embodiment, the invention provides compounds of Formula I in which A or B is a fatty acid and the remainder is a non-fatty acid molecule, compositions comprising same, mixtures of two or more thereof, and compositions comprising such mixtures. In one embodiment, the non-fatty acid molecule is selected from a non-steroidal anti-inflammatory drug (NSAID), methanesulfonic acid, niacin, difluoromethylornithine, lipoic acid, gabapentin, pre-gabalin, indomethacin, sulindac, ibuprofen, naproxen, salicylic acid, acetylsalicylic acid, salicylsalicylic, and meloxicam. In one embodiment, the non-fatty acid molecule is gabapentin. In one embodiment, the non-fatty acid molecule is an NSAID. In accordance with any of these embodiments, the fatty acid molecule may be as described above and infra. In one embodiment, the fatty acid is an omega-3 fatty acid, preferably selected from eicosapentaenoic acid (EPA), docosahexaenoic acid (DHA), and docosapentaenoic acid (DPA), and the non-fatty acid molecule is gabapentin. In one embodiment, the fatty acid is an omega-3 fatty acid, preferably selected from eicosapentaenoic acid (EPA), docosahexaenoic acid (DHA), and docosapentaenoic acid (DPA), and the non-fatty acid molecule is an NSAID.

In one embodiment, the invention provides compounds of Formula I in which A and B are each a non-fatty acid molecule, compositions comprising same, mixtures of two or more thereof, and compositions comprising such mixtures. In one embodiment, A and B are each independently selected from a non-steroidal anti-inflammatory drug (NSAID), methanesulfonic acid, niacin, difluoromethylornithine, lipoic acid, gabapentin, pre-gabalin, indomethacin, sulindac, ibuprofen, naproxen, salicylic acid, acetylsalicylic acid, salicylsalicylic, and meloxicam. In one embodiment, A and B are each gabapentin. In one embodiment, A and B are each an NSAID.

The invention also provides pharmaceutical compositions and dosage forms comprising or consisting of any of the compounds or compositions described herein. In one embodiment, the dosage form is a powder, a tablet, a capsule, a caplet, or an aqueous solution. In one embodiment, the pharmaceutical composition or dosage form further comprises one or more optional excipients as described infra. In one embodiment, the pharmaceutical composition or dosage form further comprises one or more additional active pharmaceutical agents (APIs). In one embodiment, the one or more additional APIs is selected from the group consisting of antihyperlipidemic agent, an anti-diabetic agent, an anti-epileptic agent, and an anti-inflammatory agent, and combinations thereof. In one embodiment, the one or more additional APIs is an antihyperlipidemic agent is selected from an HMG CoA enzyme inhibitor, a cholesterol absorption inhibitor, and a cholesterol esterase transfer protein (CETP) inhibitor, and combinations thereof. In one embodiment, the antihyperlipidemic agent is a statin. In one embodiment, the statin is selected from the group consisting of atorvastatin, risuvostatin, simvastatin, pravastatin, and pharmaceutically acceptable salts or prodrugs thereof.

The invention also provides a food additive or dietary supplement comprising a compound or composition of Formula I in which A or B, or both, is a fatty acid, optionally comprising a carrier suitable for administration to a human or non-human animal. In one embodiment, the food additive or dietary supplement further comprises one or more additional biologically active agents. In one embodiment, the one or more additional biologically active agents is selected from the group consisting of a vitamin, a mineral, an amino acid, a carbohydrate, an antioxidant, a flavonoid, a carotenoid, a phytoseterol, an herb, an enzyme, a botanical extract or concentrate, and a botanical compound, and combinations thereof. In one embodiment, the one or more additional biologically active agents is selected from the group consisting of vitamin A, vitamin B1, vitamin B12, vitamin B6, vitamin C, vitamin D, vitamin E, vitamin K, calcium, carnitine, chromium, chondroitin, coenzyme Q10 (ubiquinone), folate, glucosamine, metafolin, riboflavin, biotin, iodine, iron, magnesium, selenium, thiamin, and zinc, and combinations thereof.

The invention also provides unit dosage forms comprising the compounds and compositions of the invention. In one embodiment, the invention provides a unit dosage form of a compound of Formula I in which A or B, or both, is a fatty acid, or a composition comprising a mixture of two or more compounds of Formula I in which A or B, or both, is a fatty acid, the unit dosage form comprising from about 0.05 g to 12 g of total fatty acids.

The invention also provides pharmaceutical and non-pharmaceutical uses of the compounds and compositions described herein. In one embodiment, a compound or composition of the invention is useful for delivering free fatty acids, or a mixture of two or more different free fatty acids, in ionic form to a subject. In one embodiment, a compound or composition of the invention is useful for delivering free fatty acids, or a mixture of free fatty acids, in ionic form and at least one divalent metal cation selected from magnesium ($Mg^{2+}$), calcium ($Ca^{2+}$), and zinc ($Zn^{2+}$) to a subject.

In one embodiment, a compound or composition of the invention is useful for treating a disease or disorder responsive to treatment with a polyunsaturated fatty acid. In one embodiment, at least 50 wt %, at least 60 wt %, at least 70 wt %, or at least 90 wt % of the fatty acid component of the compound or composition consists of one or more omega-3 fatty acids independently selected from eicosapentaenoic acid (EPA), docosahexaenoic acid (DHA), and docosapentaenoic acid (DPA). In one embodiment, the disease or disorder is selected from a metabolic disease or disorder, a cardiovascular disease or disorder, a hematological disorder, cancer, an inflammatory disease or disorder, and a neurological disease or disorder. In one embodiment, the metabolic disease or disorder is abnormal glucose metabolism manifesting in diabetes, including type 2 diabetes, or pre-diabetes, insulin resistance, abnormal lipid metabolism manifesting as hypertriglyceridemia, i.e., elevated triglycerides, mixed dyslipidemia, hypercholesterolemia, fatty liver, and combined abnormal glucose and lipid metabolism manifesting in obesity; or a dyslipidemic disorder selected from hypertriglyceridemia, hypercholesterolemia and mixed dyslipidemias. In one embodiment, the metabolic disease or disorder is hypertriglyceridemia, severe hypertriglyceridemia, hypercholesterolemia, pre-diabetes, fatty liver disease, or obesity. In one embodiment, the cardiovascular disease or disorder is atrial fibrillation, myocardial infarction, or congestive heart failure. In one embodiment, the hematological disorder is sickle cell disease. In one embodiment, the inflammatory disease or disorder is arthritis, inflammatory bowel disease, or psoriasis. In one embodiment, the inflammatory disease or disorder is an ophthalmic inflammation disorder or dry eye syndrome. In one embodiment, the neurological disease or disorder is a psychiatric disorder selected from Alzheimer's disease, attention deficit hyperactivity disorder (ADHD) or depression. In one embodiment, the neurological disease or disorder is a neuro trauma injury selected from traumatic brain injury, spinal cord injury, ischemic stroke, or concussion.

In one embodiment, the invention provides a method for treating nociceptive pain, the method comprising administering to a subject in need of such treatment, a compound of Formula I in which A or B is a fatty acid and the remainder is a non-fatty acid molecule, or a composition comprising same. In one embodiment, the fatty acid molecule is an omega-3 fatty acid, preferably selected from eicosapentaenoic acid (EPA), docosahexaenoic acid (DHA), and docosapentaenoic acid (DPA), and the non-fatty acid molecule is gabapentin.

In one embodiment, the invention also provides a method for treating neuropathic pain, the method comprising administering to a subject in need of such treatment, a compound of Formula I in which A or B is a fatty acid and the remainder is a non-fatty acid molecule, or a composition comprising same. In one embodiment, the fatty acid molecule is an omega-3 fatty acid, preferably selected from eicosapentaenoic acid (EPA), docosahexaenoic acid (DHA), and docosapentaenoic acid (DPA), and the non-fatty acid molecule is an NSAID.

In one embodiment, the invention provides a method for treating epilepsy or epileptic syndrome, the method comprising administering to a subject in need of such treatment, a compound of Formula I in which A and B are each gabapentin.

The invention also provides for the use of a compound of Formula I in which A or B, or both, is a fatty acid, or a composition or unit dosage form comprising same, or comprising a mixture of two or more of said compounds, as a food additive or dietary supplement. In one embodiment, the use is to counter a dietary deficiency or nutritional disorder in a subject, or in a method for maintaining, promoting, or improving the general health of a subject. Accordingly, the invention provides methods of countering a dietary deficiency or nutritional disorder in a subject, as well as methods for maintaining, promoting, or improving the general health of a subject, the methods comprising administering to the subject a compound of Formula I in which A or B, or both, is a fatty acid, or a composition or unit dosage form comprising same, or a composition comprising a mixture of two or more of said compounds. In one embodiment, the composition comprises from 50 mg to 6 g of EPA, DHA, DPA, or total fatty acids, preferably total polyunsaturated fatty acids. In one embodiment, the fatty acids are omega-3, omega-6, omega-7, or omega-9 series fatty acids, or mixtures of two or more of the foregoing. In one embodiment, A and B are each omega-3 fatty acids independently selected from eicosapentaenoic acid (EPA), docosahexaenoic acid (DHA), and docosapentaenoic acid (DPA). In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA).

In one embodiment, the method is a method for improving prenatal health. In one embodiment of this method, the composition comprises from 50 mg to 6 g of DHA or total omega-3 fatty acids, and optionally further comprises one or more of a B vitamin, vitamin C, vitamin E, vitamin A, vitamin D, iron, zinc, calcium, iodine, metafolin, methylsulfonylmethane (also known as dimethyl sulfone and methyl sulfone), N-acetyl-L-cysteine, green tea extract (*Camellia sinensis*), and grape seed extract (*Vitis vinifera*). In one embodiment, the B vitamin is selected from thiamine (vitamin B-1), riboflavin (vitamin B-2), niacin (vitamin B-3), pantothenic acid (vitamin B-5), biotin (vitamin B-7), and folic acid (vitamin B-9), or any combination of the foregoing In one embodiment, the method is a method for improving heart health. In one embodiment of this method, the composition comprises from 50 mg to 6 g of EPA or total omega-3 fatty acids, and optionally further comprises one or more of coenzyme Q10, L-carnitine, an antioxidant, a phytosterol, and a flavonoid.

In one embodiment, the method is a method for improving joint health. In one embodiment of this method, the composition comprises from 50 mg to 6 g of EPA or total omega-3 fatty acids, and optionally further comprises one or more of chondroitin, glucosamine sulfate, calcium, vitamin D3, ginger extract, turmeric, curcumin, collagen, and a non-steroidal anti-inflammatory (NSAID).

In one embodiment, the method is a method for improving eye health. In one embodiment of this method, the composition comprises from 50 mg to 6 g of DHA or total omega-3 fatty acids, and optionally further comprises one or more of vitamin A, vitamin C, vitamin E, calcium, zinc, copper, selenium, a carotenoid, a flavonoid, and folic acid.

In one embodiment, the method is a method for improving cognitive health. In one embodiment of this method, the composition comprises from 50 mg to 6 g of EPA or total omega-3 fatty acids.

The invention also provides methods for making the compounds and compositions described herein. In one embodiment, the method comprises forming a mineral amino acid complex of an amino acid and a divalent metal cation (also referred to as the amino acid chelate or the mineral amino acid complex) followed by reacting the complex with molecules that will form the counter ion component, that is molecules having an acidic moiety free to complex with the basic moiety of the amino acid component. In one embodiment, the mineral amino acid complex is reacted with a mixture of free fatty acids. In one embodiment, the mineral amino acid complex is selected from magnesium di-arginate, calcium di-arginate, zinc di-arginate, magnesium di-lysinate, calcium di-lysinate, and zinc di-lysinate. In one embodiment, the mineral amino acid complex is magnesium di-lysinate. In one embodiment, the mineral amino acid complex is magnesium di-arginate. In one embodiment, the mixture of free fatty acids consists of omega-3, omega-6, omega-7, or omega-9 fatty acids, or any combination of two or more of the foregoing. In one embodiment, the mixture of free fatty acids comprises two or more, three or more, four or more, five or more, or six or more fatty acids selected from the group consisting of eicosapentaenoic acid (EPA), docosahexaenoic acid (DHA), and docosapentaenoic acid (DPA), hexadecatrienoic acid (HTA), α-Linolenic acid (ALA), stearidonic acid (SDA), eicosatrienoic acid (ETE), eicosatetraenoic acid (ETA), heneicosapentaenoic acid (HPA), tetracosapentaenoic acid, tetracosahexaenoic acid, LA, GLA, calendic acid, eicosadienoic acid, DGLA, arachidonic acid, docosadienoic acid, adrenic acid, Osbond acid, tetracosatetraenoic acid, tetracosapentaenoic acid, palmitoleic acid, vaccenic acid, paullinic acid, oleic acid, elaidic acid, gondoic acid, mead acid, erucic acid, and nervonic acid. In one embodiment, EPA and DHA are present in the mixture of free fatty acids and are present in about the same ratio to each other in both the mixture of free fatty acids and in the resulting composition. In one embodiment, EPA and DHA together make up at least 50%, at least 70%, or at least 90% of the fatty acid component of the composition.

In one embodiment, the invention provides a composition formed by the methods described herein.

BRIEF DESCRIPTION OF THE FIGURES

FIG. 4: Schematic of a specific example of a composition described herein, the composition containing a mixture of compounds of Formula IA in which A and B are each a fatty acid, and the starting blend of fatty acids contained EPA and DHA along with smaller amounts of other polyunsaturated fatty acids (PUFAs) prepared with either magnesium di-lysinate (X) or magnesium di-arginate as the amino acid component and metal component.

DETAILED DESCRIPTION OF THE INVENTION

Figure 1:
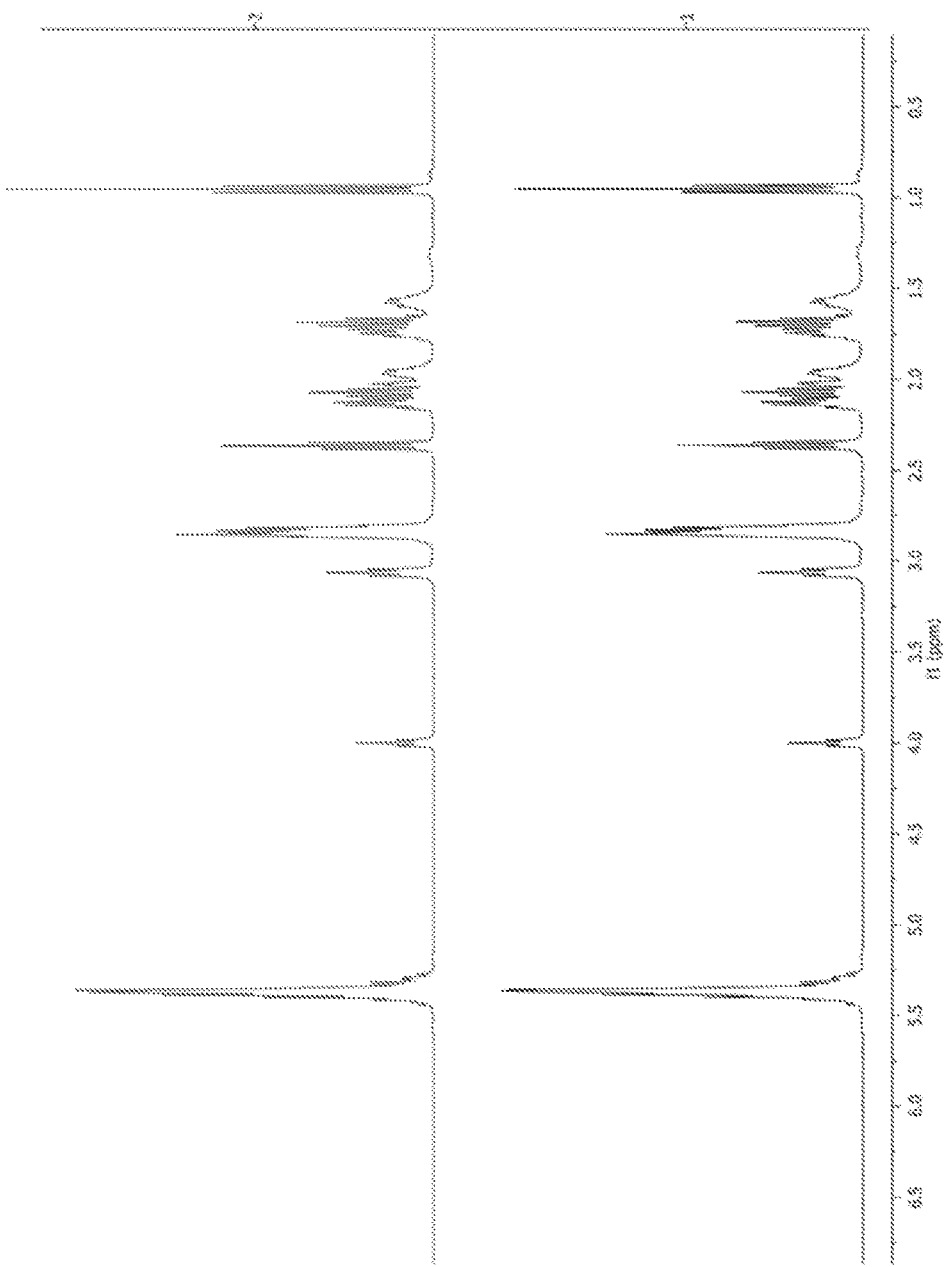
FIG. 1: Protein NMR spectrum of magnesium bis-lysinate bis-EPA taken on the day the compound was synthesized (upper trace) and 60 days later (lower trace) with the compound having been exposed to air at room temperature for the entire 60-day period.
Figure 2:
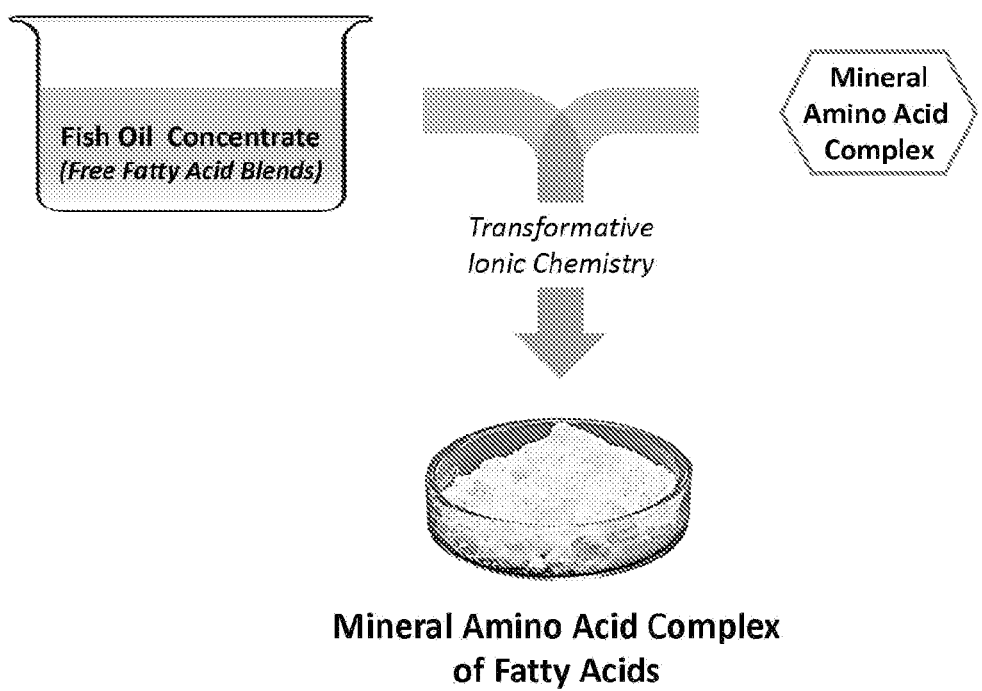
FIG. 2: General scheme for preparing a specific example of a composition described herein, the composition containing a mixture of compounds of Formula IA in which A and B are each a fatty acid.
Figure 3:
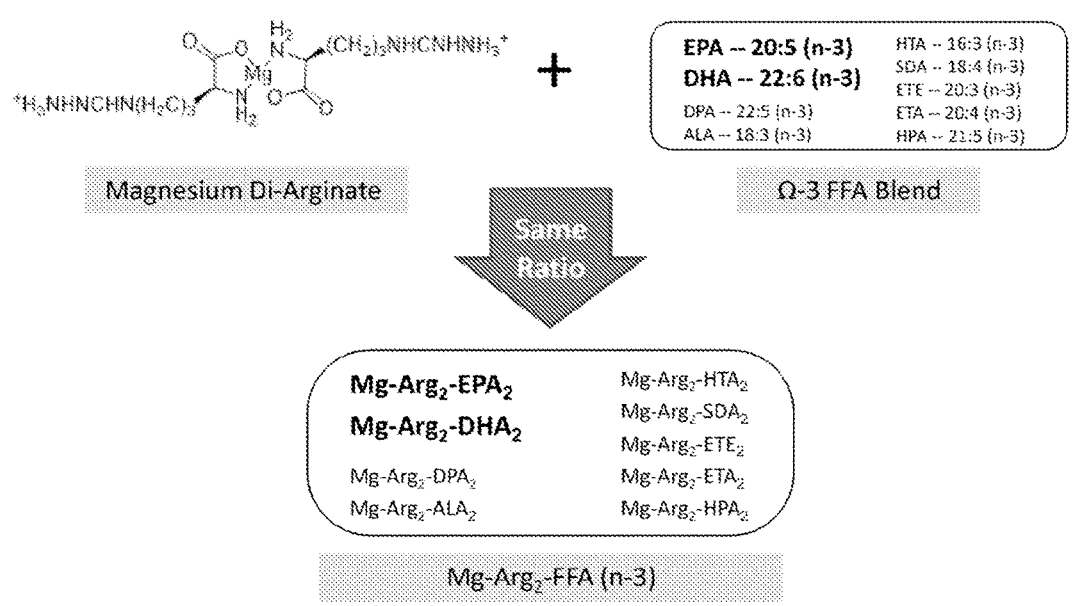
FIG. 3: Scheme for preparation of a specific example of a composition described herein, the composition containing a mixture of compounds of Formula IA in which A and B are each a fatty acid. The relative font size of the names of the free fatty acids in the starting blend represents the relative amounts of the free fatty acids in the blend. Thus, the starting blend is rich in EPA and DHA. Similarly, the resulting composition will be relatively rich in these two fatty acids (illustrated by the larger font size for magnesium di-arginate EPA and magnesium di-arginate DHA in the figure).

The invention provides compounds of Formula I and related compositions and methods. In one embodiment, the invention provides a compound of Formula I, or an enantiomer, polymorph, solvate, or hydrate thereof:

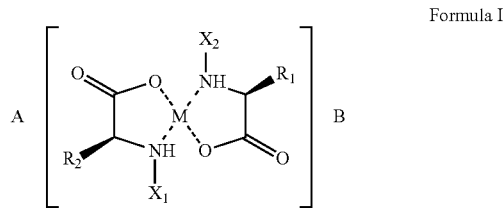

Formula I wherein $R_1$ and $R_2$ each refer to a branched or unbranched carbon chain of from 1 to 20 carbons having at least one basic function;

$R_1$ and $R_2$ are the same or different;

$X_1$ and $X_2$ are independently selected from H and —CO—Z, where Z is a peptide moiety incorporating from 1 to 5 amino acids, or a pharmaceutically acceptable salt thereof;

$X_1$ and $X_2$ are the same or different;

M is a divalent metal cation selected from magnesium ($Mg^{2+}$), calcium ($Ca^{2+}$), and zinc ($Zn^{2+}$) as the metal component; and A and B are each a molecule having at least one acidic function, either A or B, but not both, may be absent, and when both A and B are present, A and B may be the same or different.

A compound of Formula I consists of (i) an amino acid component having two amino acid moieties, each having at least one basic function in a branched or unbranched carbon chain of from 1 to 20 carbons, $R_1$, $R_2$, (ii) a divalent metal component, M, and (iii) a counter ion component consisting of one or two molecules, A, B, each having at least one acidic function. In one embodiment, each molecule of the counter ion component is an active agent, e.g., an active pharmaceutical agent or another biologically active agent, as described infra.

The invention provides both compounds of Formula I and compositions comprising same, as well as mixtures of different Formula I compounds, and compositions comprising such mixtures. In one embodiment, the invention provides compositions comprising mixtures of at least two different compounds of Formula I. In one embodiment, the mixture comprises at least 2, at least 4, at least 6, or at least 8 different Formula I compounds. In one embodiment, the mixture comprises 2, 4, 6, 8, 10, or 12 different Formula I compounds. In one embodiment, the mixtures are "pure" mixtures, meaning a mixture of two or more Formula I compounds that are prepared separately and then physically admixed together in the desired proportions. In another embodiment, the mixtures are formed from a starting mixture or blend of counter ion molecules, for example, a starting blend of fatty acids, as described infra.

The amino acid component consists of two amino acid moieties coordinated around the divalent metal component. Each amino acid moiety is coordinated around the metal component through its acidic function, e.g., its carboxyl moiety ($COO^-$). The counter-ion component is coordinated around the at least one basic function of each amino acid moiety of the amino acid component. Each amino acid moiety may comprise or consist of a single natural or non-naturally occurring amino acid, or combinations thereof; or each amino acid moiety may comprise or consist of a peptide of from 2 to 5 natural or non-naturally occurring amino acids, or combinations thereof. In either case, the amino acid moiety comprises a branched or unbranched carbon chain of from 1 to 20 carbons ($R_1$, $R_2$) having at least one basic function. Where the amino acid moiety comprises or consists of a peptide, X is —CO—Z and Z is a peptide of from 1 to 5 amino acids, or a pharmaceutically acceptable salt thereof. In one embodiment, each amino acid of the peptide is independently selected from glycine, alanine, valine, leucine, isoleucine, serine, cysteine, threonine, methionine, proline, phenylalanine, tyrosine, tryptophan, histidine, lysine, arginine, aspartic acid, glutamic acid, asparagine, and glutamine, or salts thereof. The amino salts may be, for example, the hydrochloride, citrate, tartarate, monohydrogen-, dihydrogen-, and trihydrogen phosphate, methanesufonate, benzenesulfonate and borate salt.

In one embodiment, the at least one basic function of $R_1$ and/or $R_2$ is selected from the group consisting of a primary amine, a secondary amine, a tertiary amine, and a guanidine. In one embodiment, the basic function is a primary amine. In one embodiment, the primary amine is the terminal amine of an amino acid side chain, wherein the amino acid is a natural or non-naturally occurring amino acid. In one embodiment, the amino acid is a naturally occurring amino acid selected from arginine and lysine. In one embodiment, the basic function is selected from —$NH_3+$ and —$NHC(NH_2+)NH_2$.

The two amino acid moieties of the amino acid component may be the same or different. In one embodiment, they are the same, and consistent with this embodiment, $R_1$, $R_2$, $X_1$, and $X_2$ are the same. In one embodiment, the two amino acid moieties are the same and consist of a naturally occurring amino acid selected from arginine and lysine. In one embodiment, the two amino acid moieties are the same and consist of a naturally occurring amino acid selected from arginine and lysine. In accordance with this embodiment, $R_1$ and $R_2$ are the same and each is either —$(CH_2)_4$—$NH_3+$ (lysine side chain) or —$(CH_2)_3$—$NHC(NH_2+)NH_2$ (arginine side chain). In a further aspect of this embodiment, $X_1$ and $X_2$ are the same and are hydrogen (H). In a more particular embodiment, each amino acid moiety consists of the amino acid lysine or arginine, $X_1$ and $X_2$ are the same and are hydrogen (H).

The counter ion component consists of one or two molecules, which may also be referred to as "moieties", designated A and B in Formula I, each coordinated around a basic function of an amino acid moiety. In one embodiment, either A or B is absent. Where either A or B is absent, the compound may be referred to as "mono" salt. In one embodiment, A and B are both present. Where A and B are both present, the compound may be referred to as a "bis" salt.

In one embodiment, A and B are each a fatty acid molecule and A and B are the same or different fatty acids (Formula IA). In another embodiment, A or B is a fatty acid molecule and the other molecule of the counter-ion component is a non-fatty acid molecule (Formula IB). In one embodiment, A and B are each a non-fatty acid molecule (Formula IC). In one embodiment, the non-fatty acid molecule is selected from methanesulfonic acid, niacin, difluoromethylornithine (also referred to as eflornithine), including its optical forms (e.g., D, L and racemic mixtures), lipoic acid, including its optical forms (e.g., D, L and racemic mixtures), gabapentin, pre-gabalin, indomethacin, sulindac, ibuprofen, naproxen, salicylic acid, acetylsalicylic acid, salicylsalicylic, and meloxicam. In one embodiment, the molecule is selected from salicylic acid, acetylsalicylic acid, and salicylsalicylic. In one embodiment, the non-fatty acid molecule is a therapeutic agent.

It should be understood that reference herein to a compound of Formula I includes compounds of Formulas IA, IB, and IC, each of which is a specific embodiment of a compound of Formula I.

The present invention also provides a composition comprising a compound of Formula I, Formula IA, Formula IB, or Formula IC, or a mixture of two or more thereof, and an optional carrier or excipient. In one embodiment, the composition is a pharmaceutical composition. In one embodiment, the composition is a dietary additive or supplement. The compositions of the invention are described in more detail, infra.

The invention also provides a package or kit comprising a unit dosage form of a compound or composition described herein, at least one container for holding the unit dosage form, and instructions for use.

Formulas IA and IB In one embodiment, the counter ion component comprises or consists of one or two fatty acid molecules, also referred to as fatty acid moieties or simply as fatty acids. In the context of this embodiment, the counter ion component may be referred to as the fatty acid component or the fatty acid counter ion component, interchangeably. Thus, the fatty acid component consists of one or two fatty acid moieties, A and B, each coordinated around a basic function of an amino acid moiety.

The compounds of Formula IA and Formula IB described here are different from, and advantageous over, fatty acid compositions which are in the physical form of an oily liquid which is relatively difficult to formulate and chemically susceptible to degradation, especially oxidative degradation.

The term "fatty acid" is used to describe a carboxylic acid with a long aliphatic carbon chain for from about 4 to 28 carbon atoms, which is either saturated or unsaturated, referring to whether the carbon chain contains one or more double bonds between the carbon atoms (unsaturated). In one embodiment, the fatty acid of the counter ion component in a compound of Formula IA or IB is an unsaturated fatty acid. In one embodiment, the unsaturated fatty acid is a mono-, di-, or polyunsaturated fatty acid. In one embodiment, the fatty acid is a polyunsaturated fatty acid. In one embodiment, the polyunsaturated fatty acid is a long-chain polyunsaturated fatty acid having 16 to 24 carbon atoms (C16-C24), or 20 to 22 carbon atoms (C20-C22). In one embodiment, the polyunsaturated fatty acid is a fatty acid of the omega-3, omega-6, omega-7, or omega-9 series. In one embodiment, the fatty acid is selected from a mono-, di-, or polyunsaturated fatty acid of the omega-3, omega-6, omega-7, or omega-9 series. Examples of fatty acids of the omega-3, 6, 7, and 9 series are provided in Table 1, below. In one embodiment, the fatty acid of the counter ion component in a compound of Formula IA or IB is selected from a fatty acid set forth in Table 1.

TABLE 1

Fatty acids (mono- and di-unsaturated) of the omega-3, 6, 7, and 9 series.

| Common name | Lipid name | Chemical name |
|---|---|---|
| Hexadecatrienoic acid (HTA) | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (SDA) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |
| Linoleic acid (LA) | 18:2 (n-6) | all-cis-9,12-octadecadienoic acid |
| Gamma-linolenic acid (GLA) | 18:3 (n-6) | all-cis-6,9,12-octadecatrienoic acid |
| Calendic acid | 18:3 (n-6) | 8E,10E,12Z-octadecatrienoic acid |
| Eicosadienoic acid | 20:2 (n-6) | all-cis-11,14-eicosadienoic acid |
| Dihomo-gamma-linolenic acid (DGLA) | 20:3 (n-6) | all-cis-8,11,14-eicosatrienoic acid |
| Arachidonic acid (AA) | 20:4 (n-6) | all-cis-5,8,11,14-eicosatetraenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid | 22:5 (n-6) | all-cis-4,7,10,13,16-docosapentaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |
| none | 12:1 (n-7) | 5-Dodecenoic acid |
| none | 14:1 (n-7) | 7-Tetradecenoic acid |
| Palmitoleic acid | 16:1 (n-7) | 9-Hexadecenoic acid |
| Vaccenic acid | 18:1 (n-7) | 11-Octadecenoic acid |
| Paullinic acid | 20:1 (n-7) | 13-Eicosenoic acid |
| none | 22:1 (n-7) | 15-Docosenoic acid |
| none | 24:1 (n-7) | 17-Tetracosenoic acid |
| oleic acid | 18:1 (n-9) | 9-octadecenoic acid |
| elaidic acid | 18:1 (n-9) | (E)-octadec-9-enoic acid |
| gondoic acid | 20:1 (n-9) | 11-eicosenoic acid |
| mead acid | 20:3 (n-9) | 5,8,11-eicosatrienoic acid |
| erucic acid | 22:1 (n-9) | 13-docosenoic acid |
| nervonic acid | 24:1 (n-9) | 15-tetracosenoic acid |
| Conjugated Linoleic Acids (two conjugated double bonds) | | |
| Rumenic acid | 18:2 (n-7) | 9Z,11E-octadeca-9,11-dienoic acid |
| | 18:2 (n-6) | 10E,12Z-octadeca-9,11-dienoic acid |
| Conjugated Linolenic Acids (three conjugated double bonds) | | |
| α-Calendic acid | 18:3 (n-6) | 8E,10E,12Z-octadecatrienoic acid |
| β-Calendic acid | 18:3 (n-6) | 8E,10E,12E-octadecatrienoic acid |

TABLE 1-continued

Fatty acids (mono- and di-unsaturated) of the omega-3, 6, 7, and 9 series.

| Common name | Lipid name | Chemical name |
|---|---|---|
| Jacaric acid | 18:3 (n-6) | 8Z,10E,12Z-octadecatrienoic acid |
| α-Eleostearic acid | 18:3 (n-5) | 9Z,11E,13E-octadeca-9,11,13-trienoic acid |
| β-Eleoslearic acid | 18:3 (n-5) | 9E,11E,13E-octadeca-9,11,13-trienoic acid |
| Catalpic acid | 18:3 (n-5) | 9Z,11Z,13E-octadeca-9,11,13-trienoic acid |
| Punicic acid | 18:3 (n-5) | 9Z,11E,13Z-octadeca-9,11,13-trienoic acid |
| Other | | |
| Rumelenic acid | 18:3 (n-3) | 9E,11Z,15E-octadeca-9,11,15-trienoic acid |
| α-Parinaric acid | 18:4 (n-3) | 9E,11Z,13Z,15E-octadeca-9,11,13,15-tetraenoic acid |
| β-Parinaric acid | 18:4 (n-3) | all trans-octadeca-9,11,13,15-tretraenoic acid |
| Bosseopentaenoic acid | 20:5 (n-6) | 5Z,8Z,10E,12E,14Z-eicosanoic acid |
| Pinolenic acid | 18:3 (n-6) | (5Z,9Z,12Z)-octadeca-5,9,12-trienoic acid |
| Podocarpic acid | 20:3 (n-6) | (5Z,11Z,14Z)-eicosa-5,11,14-trienoic acid |

The omega-3 and omega-6 fatty acids are commonly referred to as "essential" fatty acids because the human or animal body cannot synthesize them and therefore they must be obtained from food or other dietary sources. In one embodiment, the omega-3 fatty acid of the counter ion component in a compound of Formula IA or IB is selected from the group consisting of hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA, clupanodonic acid), docosahexaenoic acid (DHA, Cervonic acid), tetracosapentaenoic acid, 24:5 (n-3), and tetracosahexaenoic acid (Nisinic acid), 24:6 (n-3). In one embodiment, the omega-6 fatty acid of the counter ion component in a compound of Formula IA or IB is selected from the group consisting of linoleic acid (LA), gamma-linolenic acid (GLA), eicosadienoic acid, dihomo-gamma-linolenic acid (DGLA), arachidonic acid (AA), docosadienoic acid, adrenic acid, docosapentaenoic acid (Osbond acid), tetracosatetraenoic acid, and tetracosapentaenoic acid, 24:5 (n-6); and the omega-9 fatty acid of the counter ion component in a compound of Formula IA or IB is selected from the group consisting of mead acid, 20:3 (n-9), all-cis-5,8,11-eicosatrienoic acid. In one embodiment, the monounsaturated omega-9 fatty acid is selected from the group consisting of oleic acid, eicosenoic acid, erucic acid, and nervonic acid.

It is noted that docosapentaenoic acid exists as two separate analogs and each analog is in a separate fatty acid series, either the omega-3 or omega-6 series. Both compounds have the same empirical formula and molecular weight, and both have five all cis double bonds, but each differs in the position those double bonds occupy in the 22 carbon, long chain fatty acid. The omega-3 analog is commonly referred to as DPA, docosapentaenoic acid or clupanodonic acid and is all-cis-7,10,13,16,19-docosapentaenoic acid. The omega-6 analog is commonly called Osbond acid and chemically is all-cis-4,7,10,13,16-docosapentaenoic acid. Accordingly, where docosapentaenoic acid is referred to as an omega-3 fatty acid herein, all-cis-7,10,13, 16,19-docosapentaenoic acid is intended (DPA or clupanodonic acid), and where docosapentaenoic acid is referred to as an omega-6 fatty acid herein, all-cis-4,7,10,13,16-docosapentaenoic acid (Osbond acid) is intended.

Mixtures

The different compounds of Formula I may be prepared separately and then physically mixed together to form a composition comprising a physical mixture of two or more different Formula I compounds. Thus, the invention provides compositions comprising or consisting of a mixture of two or more different Formula I compounds. In various embodiments, the composition may comprise a mixture of two or more different Formula IA compounds, two or more different Formula IB compounds, two or more different Formula IC compounds, or two or more different compounds selected from any of Formula IA, IB, or IC.

In one embodiment, the invention provides methods for making mixtures of Formula IA or IB compounds by utilizing a mixture of free fatty acids as a starting material. These methods are described infra.

In one embodiment, a composition of the invention comprises or consists of a mixture of at least two different compounds of Formula IA in which A and B are the same or different fatty acids. In one embodiment, A and B are independently selected from an omega-3, omega-6, omega-7, and omega-9 fatty acid. In one embodiment, A and B comprise a mixture of omega-3 and omega-6 fatty acids. In one embodiment, the fatty acid is a monounsaturated fatty acid of the omega-9 fatty acid series.

In one embodiment, A and B are independently selected from omega-3 and omega-6 fatty acids. In one embodiment, the omega-3 and omega-6 fatty acids are independently selected from EPA, DHA, DPA, HTA, LA, GLA, DGLA, ALA, SDA, ETE, ETA, HPA, tetracosapentaenoic acid, tetracosatetraenoic acid, tetracosahexaenoic acid, calendic acid, eicosadienoic acid, arachidonic acid (AA), docosadienoic acid, Osbond acid, and adrenic acid.

In one embodiment, A and B are the same or different omega-3 fatty acids. In one embodiment, the omega-3 fatty acids are independently selected from EPA, DHA, and DPA. In one embodiment, the omega-3 fatty acids are independently selected from EPA, DHA, DPA, HTA, ALA, SDA, ETE, ETA, HPA, tetracosapentaenoic acid, and tetracosahexaenoic acid. In one embodiment, the counter-ion component comprises two omega-3 fatty acids that are the same.

In one embodiment, a composition of the invention comprising a mixture of compounds of Formula IA or IB contains from about 50 mg to 6 g of fatty acids in the fatty acid counter ion component. In one embodiment, a unit dose of such a composition comprises from about 50 mg to 6 g, or from about 500 mg to 6 g, or at least 200 mg, at least 300 mg, at least 400 mg, at least 500 mg, or at least 1 g of fatty acids, especially or particularly polyunsaturated fatty acids. In one embodiment, the fatty acid component of the composition consists of at least 70%, at least 80%, or at least 90% by weight of one or more polyunsaturated fatty acids, or from about 20% to 90%, from 30% to 90%, from 40% to 90%, from 50% to 90%, from 60% to 90%, or from 70% to 90% by weight of one or more PUFAs. In one embodiment, the fatty acids are selected from two or more of EPA, DHA, DPA, hexadecatrienoic acid (HTA), linoleic acid (LA), γ-linolenic acid (GLA), α-linolenic acid (ALA), stearidonic acid (SDA), eicosadienoic acid, eicosatrienoic acid (ETE), eicosatetraenoic acid (ETA), heneicosapentaenoic acid (HPA), tetracosapentaenoic acid, tetracosatetraenoic acid, tetracosahexaenoic acid, calendic acid, eicosadienoic acid, dihomo-gamma-linolenic acid (DGLA), arachidonic acid (AA), docosadienoic acid, adrenic acid, Osbond acid, palmitoleic acid, vaccenic acid, paullinic acid, oleic acid, elaidic acid, gondoic acid, mead acid, erucic acid, and nervonic acid. In one embodiment, the fatty acids are selected from two or more of EPA, DHA, and DPA.

In one embodiment, the invention provides a composition comprising a mixture of at least 2, at least 4, at least 6, or at least 8 different Formula IA or IB compounds. The compositions comprising mixtures of compounds of Formula IA or IB can be prepared, as described infra, to contain the desired amounts of fatty acids for particular uses. For example, the compositions can be prepared to be relatively high in one or more particular fatty acids. In certain embodiments, the compositions of the invention comprise from about 50 milligrams (mg) to about 6 grams (g) of fatty acids in the form of the fatty acid counter-ion component of the compounds of Formula IA or IB in the composition.

In one embodiment, the invention provides a composition prepared from a blend of free fatty acids containing two or more fatty acids selected from EPA, DHA, and DPA, the amounts of EPA, DHA, and DPA being present in about the same ratio to each other in both the starting blend of free fatty acids and in the final composition. In one embodiment, additional fatty acids are present in the starting blend in lesser amounts and the amount of EPA, DHA, and/or DPA together make up at least 50%, at least 70%, or at least 90% of the free fatty acids present in the blend and proportionately the same amounts in the final composition.

In one embodiment, the invention provides a composition prepared from a blend of free fatty acids containing EPA and DHA and the EPA and DHA are present in about the same ratio to each other in both the starting blend of free fatty acids and in the final composition. In one embodiment, additional fatty acids are present in the starting blend in lesser amounts and the amount of EPA and DHA together make up at least 50%, at least 70%, or at least 90% of the free fatty acids present in the blend and proportionately the same amounts in the final composition.

In one embodiment, the amount of EPA in a composition of the invention ranges from 10 to 80 wt %, based upon the total weight of the fatty acid counter ion component of the composition. In one embodiment, the amount of DHA in a composition of the invention ranges from 10 to 80 wt %, based upon the total weight of the fatty acid counter ion component of the composition. In accordance with each of these embodiments, the remainder of the weight percentage of the fatty acid counter ion component is comprised of other fatty acids which were present in lesser amounts in the starting blend of free fatty acids. In one embodiment, the remainder of the weight percentage consists of a mixture of two or more different fatty acids of the omega-3 series, the omega-6 series, the omega-7 series, or the omega-9 series, and combinations thereof. For example, the remainder of the weight percentage may consist of any combination of the fatty acids listed in Table 1. In one embodiment, the remainder of the weight percentage consists of a mixture of two or more different fatty acids selected from the group consisting of DPA, HTA, ALA, SDA, ETE, ETA, HPA, tetracosapentaenoic acid, and tetracosahexaenoic acid.

In one embodiment, the free fatty acids in the starting blend or in the fatty acid counter ion component of a composition described herein comprise two or more different fatty acids from among the fatty acids listed in Table 1, and combinations thereof.

Physical Properties

Generally, the compounds and compositions of the invention provide a physically and chemically stable form of the molecules comprising the counter ion component. Physically, the compounds and compositions of the invention are solid, free flowing substances suitable for formulation into solid dosage forms such as powders, tablets, capsules or caplets. The solid, free-flowing character of the compositions of the invention also provides for ease of their formulation in physical admixture with each other and with other active agents in the same solid dosage form. In one embodiment, the solid dosage form is adapted for oral delivery.

The compounds of Formula I generally possess superior chemical and physical stability of the counter ion component, for example as compared to the free form of the counter ion molecules. For example, in the embodiments of Formula I in which either A or B, or both, is a fatty acid (Formula IA and IB), the fatty acid component has superior chemical stability compared to fatty acid formulations based upon the oil form of the fatty acid, e.g., the free fatty acids or the ethyl ester or glyceryl ester forms of the fatty acids. Since the compounds of Formula IA and IB, and the compositions comprising same or mixtures of same, described herein are solids (not oils) and they are very stable against oxidative degradation of the fatty acid component, particularly when compared to the free fatty acid or fatty acid ester forms of the fatty acids, which are highly susceptible to oxidative degradation in their liquid forms and consequently tend to degrade when exposed to air or humidity. In contrast, the compounds of Formula IA and IB, and the compositions comprising same or mixtures of same, are, for example, relatively more stable to air, oxygen, and humidity compared to compounds and compositions comprising the free fatty acids or the ethyl ester or glyceryl ester forms of the fatty acids. This is evidenced, for example by no significant change in physical properties, such as flow characteristics, or in chemical properties, as measured by NMR spectroscopy, following days of storage in an open vial at room temperature and standard humidity, for example following from about 7 to 14 days or up to 30, up to 60, or up to 90 days of storage.

The compounds of Formula I may also provide improved bioavailability of the counter ion component compared to other dosage forms of the molecules comprising the counter ion component. For example, where the counter ion component comprises or consists of fatty acid molecules, the bioavailability of the fatty acid molecules is increased as compared to, for example, free fatty acids and esters of the fatty acids.

The compounds of Formula I may also provide for more favorable pharmacokinetic properties of the counter ion component compared to the pharmacokinetic properties of other dosage forms of the molecules comprising the counter ion component. The advantageous pharmacokinetics of the compounds of Formula I relate, in part, to their advantageous property of completely dissociating into their component ionic species (e.g., ionic forms of the metal component, the amino acid component, and the counter ion component) upon immersion in aqueous media at low pH (such as gastric or gastrointestinal fluid, e.g., within a pH range of from about 6.0 to below 1.0). In general, the compounds of Formula I are sparingly soluble or nearly insoluble in water at physiological pH and are also insoluble in most organic solvents. However, they are soluble in aqueous acidic media where the pH is about 6 or less. Thus, when a compound of the invention is immersed in aqueous media of low pH, the counter-ion component dissociates into its ionic form, e.g., for Formula IA and IB compounds, the ionic forms of the free fatty acids. The compounds of the invention are therefore useful for delivering the counter ion component, such as fatty acids, in their ionic form, to a human or animal subject.

The compounds of Formula I may also provide for high bioavailability of the mineral component by enabling its efficient absorption in the gastrointestinal tract.

The compounds of the invention may also provide for increased water solubility and/or stability of a molecule of the counter-ion component compared to the molecule itself. In one embodiment, the compounds of the invention allow for the systemic delivery of higher amounts of a poorly water soluble molecule in the counter-ion component, when administered to a subject, for example by an oral, as compared to the molecule itself. In some embodiments, the molecule of the counter-ion component also has increased bioavailability when administered by an oral, as compared to the molecule itself.

Compositions

The invention provides compositions comprising a compound of Formula I, Formula IA, Formula IB, or Formula IC, and compositions comprising mixtures of two or more different Formula I, Formula IA, Formula IB, or Formula IC compounds.

In one embodiment, the invention provides compositions comprising a compound of Formula I and compositions comprising mixtures of two or more different Formula I compounds.

In one embodiment, the invention provides compositions comprising a compound of Formula IA and compositions comprising mixtures of two or more different Formula IA compounds.

In one embodiment, the invention provides compositions comprising a compound of Formula IB and compositions comprising mixtures of two or more different Formula IB compounds.

In one embodiment, the invention provides compositions comprising a compound of Formula IC and compositions comprising mixtures of two or more different Formula IC compounds.

The composition may be formulated as a solid dosage form selected from a powder, tablet, capsule, or caplet. In one embodiment, the solid dosage form is adapted for oral delivery. In one embodiment, the solid dosage form is adapted for once a day delivery. In another embodiment, the solid dosage form is adapted for delivery twice a day. In one embodiment, the dosage form is an oral dosage form. The oral dosage form may be in the form of a solid, such as a tablet, a capsule containing particulates, liquids, or powders, a lozenge (including liquid-filled), a gum, or a gel, or in the form of a liquid. In one embodiment, the pharmaceutical composition of the invention is formulated as a gel or cream suitable for topical administration. In one embodiment, the dosage form is a solid oral dosage form.

In one embodiment, the composition is a pharmaceutical composition and the carrier is acceptable for administration to humans or non-human animals, as described in more detail infra.

In one embodiment, the composition is a dietary supplement or additive and the carrier is acceptable for administration to humans or non-human animals, as described in more detail infra.

A composition of the invention may be in the form of a unit dose. The unit dose may be, for example, in the form of a tablet or capsule. In one embodiment, the composition comprises a compound of Formula IA or IB, or a mixture of two or more different Formula IA or IB compounds. In one embodiment, a unit dose of the composition contains from about 0.05 g to 12 g of total fatty acids. In one embodiment, the unit dose contains from about 0.05 g, 1 g, 2 g, 3 g, 4 g, 5 g, or 6 g of total fatty acids.

The compounds described here may be formulated alone or in combination with one or more additional active pharmaceutical ingredients (API) or biologically active agents. In one embodiment, a compound described here is formulated with one or more additional APIs or biologically active agents in a single dosage form, preferably a solid dosage form.

Depending on the nature of the compounds and excipients making up the composition, the composition may be suitable for pharmaceutical or veterinary use, or for use a dietary additive or supplement, or any combination of these uses. The various compositions are discussed in the following sections as "pharmaceutical compositions" and "additives and supplements" but these terms are not meant to be limiting, only descriptive.

The compositions of the invention may be formulated using one or more suitable excipients or carriers. A suitable excipient or carrier is one suitable for human or animal use. The term "excipient" refers to an additive that serves some purpose in the composition other than a carrier, for example as a stabilizer, taste masking agent (e.g., a sweetener), solubilizing agent, or suspending agent. Often, a carrier will serve a dual purpose as a simple carrier or diluent and an excipient. Examples of pharmaceutically acceptable excipients may thus include carriers. Non-limiting examples of excipients for use in the compositions of the invention include sterile liquids, water, buffered saline, ethanol, polyols (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures thereof.

A suitable excipient or carrier is typically a pharmaceutically acceptable carrier or excipient for use in animals or humans (or both). The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. In the context of the pharmaceutical compositions of the invention, a "carrier" refers to, for example, a solvent, a diluent, or vehicle with which the ionic salt of the invention is formulated for delivery. Examples of pharmaceutically acceptable carriers for use in the compositions of the invention include, without limitation, sterile aqueous and non-aqueous liquids, water, buffered saline, ethanol, polyols (for example, glycerol, propylene glycol, liquid polyethylene glycol and the like), and oils, for liquid dosage forms; or carbohydrates (e.g., glucose, lactose, sucrose or dextran) for solid dosage forms.

The compounds of the invention may be formulated in any suitable form and for any suitable intended route of administration. Typically, the dosage form is at least in part determined by the intended route of administration.

In one embodiment, the dosage form is a liquid suitable for administration to the eye. The formulation may be a solution, suspension, or gel suitable for ocular administration, e.g., suitable for topical administration to the eye, also referred to as an ophthalmic formulation.

In one embodiment, the ophthalmic formulation is an aqueous formulation. In one embodiment, the ophthalmic formulation comprises one or more of glycerin, hypromellose, propylene glycol or polyethylene glycol. In one embodiment, the ophthalmic formulation further comprises one or more of polysorbate 80, carbomer copolymer type A, purified water, sodium hydroxide, ascorbic acid, benzalkonium chloride, boric acid, dextrose, disodium phosphate, glycine, magnesium chloride, potassium chloride, sodium borate, sodium chloride, sodium citrate, sodium lactate, edetate disodium, hydrochloric acid, sodium hydroxide, aminomethylpropanol, hydroxypropyl guar, polyquaternium-I, or sorbitol.

In one embodiment, the ophthalmic formulation comprises one or more of surfactants, tonicity agents, buffers, preservatives, co-solvents and viscosity building agents. Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Preferably, the tonicity agent is present in an amount sufficient to cause the final composition to have an ophthalmically acceptable osmolality (generally about 150-450 mOsm, preferably 250-350 mOsm). An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6-7.5.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more of the fatty acid salts of the invention.

Examples or artificial tears compositions useful as artificial tears carriers include, but are not limited to, commercial products, such as Tears Naturale™, Tears Naturale N™, Tears Naturale Free™, and Bion Tears™. (Alcon Laboratories, Inc., Fort Worth, Tex.). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Gionek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as polyvinyl alcohol, polyvinylpyrrolidone, povidone and carbomers, such as carbomer 934P, carbomer 941, carbomer 940, carbomer 974P.

Examples of viscosity enhancing agents include, but are not limited to polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears will exhibit a viscosity of 1 to 400 centipoises ("cps"). Topical ophthalmic products are typically packaged in multidose form. Preservatives may be required to prevent microbial contamination during use. Suitable preservatives include benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Other wetting agents, emulsifiers and lubricants, such as sodium lauryl sulfate and magnesium stearate, as well as coloring agents, release agents, coating agents, and perfumingagents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, a-tocopherol, and the like; and metal chelating agents, such as citric acid, ethylenediamine tetraacetic acid (EDTA), sorbitol, tartaric acid, phosphoric acid, and the like.

A contact lens may optionally be used to allow for extravasation of vasoactive substance over a more prolonged time period. Vasoactive substances such as Thrombin and Thromboxane A may further induce increase in tear volume via venular vasoconstriction and increased perfusion through lacrimal, accessory lacrimal and surface microvessels; where increased paracellular endothelial openings that increase capillary permeability can further enhance this benefit.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers.

Pharmaceutical Compositions

In one embodiment, the composition is a pharmaceutical composition comprising a compound of Formula I, Formula IA, Formula IB, or Formula IC, or a mixture thereof, and a pharmaceutically acceptable carrier and/or excipient.

In one embodiment, the invention provides a solid dosage form comprising a composition of the invention in physical admixture with one or more additional active pharmaceutical ingredients (APIs). In one embodiment, the one or more additional APIs is an antihyperlipidemic agent, an anti-diabetic agent, an anti-epileptic agent, or an anti-inflammatory agent. In one embodiment the API is an antihyperlipidemic agent or an anti-diabetic agent. In one embodiment, the antihyperlipidemic agent is selected from the group consisting of an HMG CoA enzyme inhibitor (e.g., a statin), a cholesterol absorption inhibitor, and a cholesterol esterase transfer protein (CETP) inhibitor. In one embodiment, the antihyperlipidemic agent is a statin. In one embodiment, the statin is selected from the group consisting of atorvastatin, risuvostatin, simvastatin, pravastatin, and pharmaceutically acceptable salts or prodrugs thereof. In one embodiment, the statin is present in an amount ranging from 5 mg to 100 mg. In one embodiment, the statin is pravastatin. In one embodiment, the antihyperlipidemic agent is a cholesterol absorption inhibitor. In one embodiment, the cholesterol absorption inhibitor is ezetimibe, also known as Zetia. In one embodiment, the antihyperlipidemic agent is a CETP inhibitor. In one embodiment, the CETP inhibitor is anacetrapib, or a hydrate, or solvate thereof.

In one embodiment, the composition is a pharmaceutical composition effective to lower elevated serum triglycerides in a subject, preferably a human subject. In one embodiment, the pharmaceutical composition comprises a compound of Formula IA or IB, a mixture of compounds of Formula IA, a mixture of compounds of Formula IB, or mixtures of any of the foregoing. In one embodiment, the subject is a human subject having severe hypertriglyceridemia. In one embodiment, the subject is a human subject having non-severe hypertriglyceridemia.

In one embodiment, the composition is a pharmaceutical composition effective to treat a metabolic disorder selected from the group consisting of abnormal glucose metabolism manifesting in diabetes or pre-diabetes, abnormal lipid metabolism manifesting as hypertriglyceridemia, i.e., elevated triglycerides, mixed dyslipidemia, fatty liver, and combined abnormal glucose and lipid metabolism manifesting in obesity. In one embodiment, a composition of the invention is used in a method for treating a disease or disorder selected from diabetes, pre-diabetes, hypertriglyceridemia, dyslipidemia, fatty liver, and obesity. In one embodiment, the pharmaceutical composition comprises a compound of Formula IA or IB, a mixture of compounds of Formula IA, a mixture of compounds of Formula IB, or mixtures of any of the foregoing.

In one embodiment, the composition is a pharmaceutical composition effective to treat a disease or disorder selected from the group consisting of arthritis, irritable bowel syndrome, atrial fibrillation, ophthalmic inflammation disorders, dry eye syndrome, traumatic brain injury, familial adenomatous polyposis, sporadic adenomatous polyposis, epilepsy, epileptic syndrome, Alzheimer's disease, and attention deficit hyperactivity disorder (ADHD). In one embodiment, the pharmaceutical composition comprises a compound of Formula IA or IB, a mixture of compounds of Formula IA, a mixture of compounds of Formula IB, or mixtures of any of the foregoing. In one embodiment, the pharmaceutical composition comprises a compound of Formula IC, a mixture of compounds of Formula IC.

In one embodiment, the composition is a pharmaceutical composition effective to treat or manage pain in a subject. In one embodiment, the pain is neuropathic pain or nociceptive pain. In one embodiment, the pharmaceutical composition comprises a compound of Formula IB or IC, a mixture of compounds of Formula IB, a mixture of compounds of Formula IC, or mixtures of any of the foregoing.

Particular compounds for use in treating the various diseases and disorders referred to here are described in more detail infra.

Non-Pharmaceutical Compositions

The compositions of the invention may also be formulated with one or more additional non-pharmaceutical agents, for example beneficial biologically active agents, such as a nutrient or nutraceutical compounds, including e.g., vitamins, minerals, botanical extracts, etc., in the same dosage form, along with any suitable excipients or carriers. In one embodiment, the one or more additional biologically active agents is selected from the group consisting of a vitamin, a mineral, an amino acid, a carbohydrate, an antioxidant, a flavonoid, a carotenoid, a phytoseterol, an herb, an enzyme, a botanical extract or concentrate, and a botanical compound. In one embodiment, the one or more additional biologically active agents is selected from the group consisting of vitamin A, vitamin B1, vitamin B12, vitamin B6, vitamin C, vitamin D, vitamin E, vitamin K, calcium, carnitine, chromium, chondroitin, coenzyme Q10 (ubiquinone), folate, glucosamine, metafolin, riboflavin, biotin, iodine, iron, magnesium, selenium, thiamin, and zinc. In one embodiment, the one or more additional biologically active agents is selected from the group consisting of coenzyme Q10, L-carnitine, an antioxidant, a phytoseterol, and a flavonoid. In one embodiment, the antioxidant is a polyphenol. In one embodiment, the polyphenol is selected from lycopene, resveratrol, and epigallocatechingallate.

In one embodiment, A or B, or both are useful as a dietary supplement or nutraceutical additive. For example, fatty acids, especially polyunsaturated fatty acids of the omega-3, omega-6, omega-7, and omega-9 series are known to be useful in this context. Thus, the invention also provides a compound of Formula I formulated as a nutraceutical additive or supplement, either alone or in combination with one or more additives or supplements and any suitable excipients. In one embodiment, the nutraceutical additive or supplement is in the form of a powder. In one embodiment, the nutraceutical additive or supplement is in the form of a liquid. In one embodiment, the nutraceutical additive or supplement is in the form of a mouth wash, a dentifrice, chewing gum, a candy, a tablet, a capsule, a mouth spray, or a film.

In one embodiment, the nutraceutical additive forms part of a food or drink product suitable for human consumption. There is no specific limitation on the foods/drinks to which a nutraceutical additive of the invention can be incorporated. Examples of such foods/drinks include processed foods based on meat, poultry meat, fish/shellfish and the like; soup; seasonings including sweetener and the like; rice seasonings; instant foods; frozen foods; snacks; various types of functional foods such as supplements, nutritional drinks and the like; canned foods; dairy products; confectionery such as chewing gum, candy, gummy candy, chocolate, baked sweets and the like; ice cream; soft drinks such as tea, coffee, cocoa, fruit juice, sports drink, carbonated drink, vegetable drink and the like; liquors; soya milk; lactic acid bacteria beverages; and chlorophyll juice.

The amount of the nutraceutical additive of the invention incorporated into the food or drink varies in accordance with the type of food or drink and the amount that one wishes to supplement a diet with one or more omega-3 fatty acids. In one embodiment, the nutraceutical additive is incorporated into the food or drink so as to provide an amount of the omega-3 fatty acid that is about 0.000001 to 20% by weight, based on total weight of the food or drink product, and more preferably in an amount of about 0.00001 to 10% by weight.

Methods of Making

The present invention is based in part upon Applicant's discovery of a unique process for making a mineral amino acid salt of a biologically active agent which is effective to provide the active agent in a physical form having superior properties, for example, improved chemical and/or physical stability, and/or improved bioavailability, compared with the free forms (or other salt forms) of the active agent. For example, in one embodiment, the biologically active agent is a fatty acid and the mineral amino acid fatty acid salts of the invention are effective to transform an oily liquid of, e.g., free fatty acids, into a free flowing solid that is more physically and chemically stable that the free fatty acids themselves, and also shows improved bioavailability of the fatty acid compared to the free fatty acids themselves as well as compared to the ethyl ester or glyceryl ester forms of the fatty acids.

The compounds of Formula I are prepared by reacting a metal cation (M) with an amino acid (or mixture of two or more different amino acids) in a 1:2 molar ratio to produce a mineral amino acid complex (chelate) in which the amino acids are complexed around the metal cation in a 2:1 amino acid to metal ratio. The amino acids used to form the compounds of Formula I may be any natural or non-naturally occurring amino acids, or combinations thereof, provided that the amino acids contain at least one basic function that is available for reacting with the counter-ion molecule or molecules after the mineral amino acid complex has formed. To form the compounds of Formula I, the mineral amino acid complex is reacted with the counter ion molecule or molecules that will form the counter ion component. In one embodiment, the counter ion component consists of one or two molecules independently selected from a fatty acid molecule and a non-fatty acid molecule. In one embodiment, the non-fatty acid molecule is selected from the non-fatty acid molecule is selected from methanesulfonic acid, niacin, difluoromethylornithine (also referred to as eflornithine), including its optical forms (e.g., D, L and racemic mixtures), lipoic acid, including its optical forms (e.g., D, L and racemic mixtures), gabapentin, pre-gabalin, indomethacin, sulindac, ibuprofen, naproxen, salicylic acid, acetylsalicylic acid, salicylsalicylic, and meloxicam. In one embodiment, the molecule is selected from salicylic acid, acetylsalicylic acid, and salicylsalicylic. In one embodiment, the non-fatty acid molecule is a therapeutic agent.

A composition comprising a mixture of compounds of Formula IA or IB, (A and B are each a fatty acid, or at least one of A or B is a fatty acid) may be prepared by reacting the mineral amino acid complex with, e.g., a blend of two or more different free fatty acids in e.g., a 1:2 molar ratio to form a composition comprising a mixture of different compounds of Formula I, each having fatty acid counter-ions A and B, which may be the same or different in any particular compound of the composition. The relative amounts of the different fatty acids to each other in the composition will generally be about the same as their relative amounts to each other in the starting blend of free fatty acids. Where the starting material is a mixture of free fatty acids, the solid composition retains the same relative amounts of fatty acids that were present in the original mixture (the terms "mixture" and "blend" are used interchangeably herein). As described in more detail below, the invention also provides methods that can be used to produce a free flowing powder composition comprising a mixture of fatty acids having any desired ratio of two or more different fatty acids to each other. A "pure" compound of Formula IA can also be prepared by reacting the mineral amino acid complex with a single free fatty acid, instead of a blend of different free fatty acids, in order to produce a compound in which A and B are the same. Using this process, different compounds of Formula IA (e.g., having a different fatty acid component where A and B are the same) can be produced and then mixed together to form a composition having precise amounts of the different fatty acids in the counter ion component.

The compositions may be mono- or bis-salts of the fatty acids with the mineral amino acid complex. Preferably, they are bis-salts, meaning that A and B of Formula I are both present in the composition. If a single species of mineral amino acid complex is reacted with the blend of free fatty acids, the resulting mixture of compounds of Formula IA will each have the same peptide component and metal component and will differ only in their counter-ion components, i.e., in the fatty acids, A and B of Formula IA. In one embodiment, the mineral amino acid complex is selected from magnesium di-arginate, calcium di-arginate, zinc di-arginate, magnesium di-lysinate, calcium di-lysinate, and zinc di-lysinate. In one embodiment, the blend of free fatty acids comprises at least two, at least four, at least 6, or at least 8 fatty acids selected from the group consisting of mono-, di-, and poly unsaturated fatty acids, and combinations thereof. In one embodiment, the fatty acids are selected from the group consisting of EPA, DHA, DPA, hexadecatrienoic acid (HTA), linoleic acid (LA), g-linolenic acid (GLA), α-linolenic acid (ALA), stearidonic acid (SDA), eicosadienoic acid, eicosatrienoic acid (ETE), eicosatetraenoic acid (ETA), heneicosapentaenoic acid (HPA), tetracosapentaenoic acid, tetracosatetraenoic acid, tetracosahexaenoic acid, calendic acid, eicosadienoic acid, dihomo-gamma-linolenic acid (DGLA), arachidonic acid (AA), docosadienoic acid, adrenic acid, Osbond acid, palmitoleic acid, vaccenic acid, paullinic acid, oleic acid, elaidic acid, gondoic acid, mead acid, erucic acid, and nervonic acid.

The starting blend of free fatty acids for use in making the compositions of the invention may be derived from natural sources such as fish oil, seed oil, krill oil, microbial oils; esters of fish oil, seed oil, krill oil, egg oil, marine algae, squid oils, walnut oil, edible seed oil, clary sage seed oil, algal oil, flaxseed oil, Sacha Inchi oil, Echium oil, hemp oil, microbial oils; or triglycerides resulting from re-esterification of purified esters from fish oil, seed oil, krill oil, or microbial oils.

The starting blend of free fatty acids for use in making the compositions of the invention may also be obtained from commercial sources, in which the crude natural oil, or its esters and re-esterified products, have been saponified, or in some cases enhanced with fatty acids such as DHA or EPA. Suitable sources of free fatty acid blends for use as starting materials in making the compositions of the invention include, without limitation, free fatty acid blends available from BASF SE (Germany), Croda International plc (United Kingdom), Epax Norway AS (Norway), KD-Pharma Bexbach GmbH (Germany), Nippon Suisan Kaisha, Ltd. (Japan), KinOmega Biopharm Inc. (China), Chemport Inc. (Korea), Wuxi Xunda Marine Biological Products Co., Ltd. (China), Naturmega S.A. (Colombia), and Omega Protein Corp. (USA). Other commercial sources of fatty acids and fatty acid blends will be known to the skilled person and can be used as starting materials in making the compositions described here. Combinations of free fatty acids from multiple sources may also be used, for example, to create a custom blend of free fatty acids. Importantly, any starting blend of free fatty acids, whether derived from natural or commercial sources, or a combination thereof, can be used in making the compositions of the invention. In certain embodiments, the blend is selected or created in order to achieve predetermined amounts of particular fatty acids in the compositions of the invention. For example, in order to produce a blend that is high in one or more particular fatty acids.

Preferably, the fatty acids comprising the blend for making the compositions described herein are polyunsaturated fatty acids (also referred to as "PUFAs"). The term polyunsaturated fatty acids as used in the present disclosure may refer collectively to mono-, di-, and polyunsaturated fatty acids. A polyunsaturated fatty acid of, for example, the omega-3 series, may also be referred to interchangeably as an "omega-3 fatty acid", and similar terminology may be applied to other series, such as the omega-6, omega-7, and omega-9 series. Non-limiting examples of the fatty acids that may comprise the blend of free fatty acids used to make the compositions of the invention, and therefore which also will form the fatty acid counter ion component of those compositions, are listed in Table 1.

Preferably, for use in making the compositions described here, the starting blend of free fatty acids is of high purity with respect to one or more particular classes of fatty acids, e.g., omega-3 fatty acids, omega-6 fatty acids, omega-7 fatty acids, or omega-9 fatty acids, or a mixture of any of the foregoing. In one embodiment, the starting blend is of high purity with respect to omega-3 fatty acids, for example 60% to 99% omega-3 fatty acid, preferably 70% to 99%, 80% to 99%, or greater than 95% omega-3 fatty acid. The starting blend is also preferably substantially free or contains minimal amounts of impurities such as oxidative impurities, dioxins and furans, heavy metals such as arsenic, cadmium, lead, and mercury, polyaromatic hydrocarbons, polychlorinated biphenyls (PCBs), and dioxin-like-PCBs.

As discussed above, in addition to commercially available free fatty acid blends, or those that may be attainable through specific purification processes, or from microbial processes, one can create a custom blend of free fatty acids for use in making the compositions of the invention. In general, any blend can be chosen to give the desired proportions of fatty acids in the resulting compositions because the compositions will retain the same relative amounts of fatty acids as were present in the starting blend. Thus, the proportional amount of a particular fatty acid (or fatty acids) in the counter-ion component of the compositions described here can be adjusted by adjusting its amount in the starting blend of free fatty acids, or by choosing a blend that has the desired proportional amount of one or more particular fatty acids. For example, a starting blend of free fatty acids consisting of fatty acid A and fatty acid B in a ratio of 3:1, respectively, would yield a composition of the invention also comprising fatty acid A and fatty acid B in proportionally the same amounts of 3:1. Therefore, the relative amounts (described either as percentages or weight ratios) of the different free fatty acids in the starting blend will determine the relative amounts of those fatty acids making up the counter ion component of the resulting composition. In one embodiment, the starting blend is chosen such that the relative amounts of EPA and DHA are higher than other fatty acids in the blend. In one embodiment, the amount of EPA and DHA in the starting blend of fatty acids is from 10:80 to 80:10, with the remainder comprised of other fatty acids of the omega-3 series, such as DPA, HTA, ALA, SDA, ETE, ETA, HPA, tetracosapentaenoic acid, and tetracosahexaenoic acid, omega-6, 7 and/or 9 series (see e.g., Table 1).

Also provided are methods of making the compositions described herein, the methods comprising forming an amino acid chelate of an amino acid and a divalent metal followed by reacting the amino acid chelate with a mixture of free fatty acids. In one embodiment, the amino acid chelate is selected from magnesium di-arginate, calcium di-arginate, zinc di-arginate, magnesium di-lysinate, calcium di-lysinate, and zinc di-lysinate. In one embodiment, the amino acid chelate is magnesium di-arginate. In one embodiment, the mixture of free fatty acids comprises two or more, three or more, four or more, five or more, or six or more fatty acids. In one embodiment, the fatty acids are selected from mono-, di-, and polyunsaturated fatty acids, and combinations thereof. In one embodiment, the fatty acids are selected from omega-3, omega-6, omega-7, and omega-9 fatty acids, and combinations thereof. In one embodiment, the fatty acids are selected from omega-3 and omega-6 fatty acids, and combinations thereof. In one embodiment, the fatty acids are selected from the group consisting of eicosapentaenoic acid (EPA), docosahexaenoic acid (DHA), and docosapentaenoic acid (DPA), hexadecatrienoic acid (HTA), α-linolenic acid (ALA), stearidonic acid (SDA), eicosatrienoic acid (ETE), eicosatetraenoic acid (ETA), heneicosapentaenoic acid (HPA), tetracosapentaenoic acid, tetracosatetraenoic acid, tetracosahexaenoic acid, calendic acid, eicosadienoic acid, DGLA, AA, docosadienoic acid, adrenic acid, Osbond acid, palmitoleic acid, vaccenic acid, paullinic acid, oleic acid, elaidic acid, gondoic acid, mead acid, erucic acid, and nervonic acid.

In one embodiment, the method comprises forming an amino acid chelate of an amino acid and a divalent metal followed by reacting the amino acid chelate with a mixture of omega-3 free fatty acids. In one embodiment, the amino acid chelate is selected from magnesium di-arginate, calcium di-arginate, zinc di-arginate, magnesium di-lysinate, calcium di-lysinate, and zinc di-lysinate. In one embodiment, the amino acid chelate is magnesium di-arginate. In one embodiment, the mixture of omega-3 fatty acids comprises two or more, three or more, four or more, five or more, or six or more of EPA, DHA, DPA, HTA, ALA, SDA, ETE, ETA, HPA, tetracosapentaenoic acid, and tetracosahexaenoic acid. In one embodiment, the mineral is selected from magnesium (Mg2+), calcium (Ca2+), or zinc (Zn2+).

Methods of Use

The compositions of the invention are useful in methods of treating various diseases and disorders that are responsive to treatment with the molecules forming the counter ion component of a compound of Formula I, or mixtures thereof. In addition, the compositions of the invention may have non-pharmaceutical uses, for example as dietary supplements or additives. These uses are described in more detail infra.

In one embodiment, where the compound is of Formula IA or IB, the methods relate to diseases and disorders that are responsive to treatment with fatty acids, especially polyunsaturated fatty acids, and particularly polyunsaturated fatty acids of the omega-3, omega-6, omega-7, and omega-9 series. The methods relating to diseases or disorders that are responsive to treatment with fatty acids, discussed in more detail infra, encompass the use of compounds of Formula IA and IB, and compositions comprising mixtures of the compounds of Formula IA, mixtures of the compounds of Formula IB, or mixtures of both IA and IB.

In accordance with any of the following embodiments (including both pharmaceutical and non-pharmaceutical uses) having a fatty acid moiety in the counter-ion component, A and B may each independently be selected from a fatty acid of the omega-3, omega-6, omega-7, or omega-9 series, including any of the fatty acids set forth in Table 1, and combinations thereof, as described supra. In one embodiment, at least 50%, at least 60%, at least 70%, at least 80%, or at least 90% of the fatty acid component of a composition comprising compounds of Formula IA and/or IB consists of one or more omega-3 fatty acids independently selected from eicosapentaenoic acid (EPA), docosahexaenoic acid (DHA), and docosapentaenoic acid (DPA).

In the context of any of the methods described here, a composition of the invention may be formulated as a pharmaceutical composition, or as a food additive or supplement, meaning that the composition itself and any additives or excipients in the formulation are suitable for administration to humans or animals.

In the context of the methods described here, the term "treating" may refer to the amelioration or stabilization of one or more symptoms associated with the disease or disorder. The term "treating" may also encompass the management of a disease or disorder, referring to the beneficial effects that a subject derives from a therapy which does not result in a cure of the underlying disease or disorder. For example, lowering elevated plasma triglycerides can be considered an aspect of treating diabetes because it is a beneficial effect that does not result in a cure of the underlying defect of glucose metabolism. The compositions of the invention can also be used in the prevention of certain diseases, disorders, and conditions. In this context, the term "prevention" refers to preventing the recurrence, development, progression or onset of one or more symptoms of the disease, disorder, or condition.

In accordance with the methods of the invention, a therapeutically effective amount of a composition of the invention is administered to a subject, the therapeutically effective amount being the amount sufficient to achieve a desired therapeutic outcome, for example the amelioration or stabilization of one or more symptoms of the disease or disorder being treated, or in the context of prevention, the amount sufficient to achieve prevention of the recurrence, development, progression or onset of one or more symptoms of the disease, disorder, or condition.

For administration to human patients, the total daily dose of the compounds of the invention is typically in the range 50 mg to 12 g depending, of course, on the route of administration. In one embodiment the total daily dose is in the range of from about 100 mg to 500 mg, about 500 mg to 1 g, about 1 g to 2 g, about 2 g to 5 g, or about 5 g to 10 g. In another embodiment the total daily dose is in the range 4 g to 8 g and in yet another embodiment the total daily dose is in the range 1 g to 2 g. The total daily dose may be administered in single or divided doses.

These dosages are based on an average human subject having a weight of about 65 kg to 70 kg. The physician will readily be able to determine doses for subjects whose weight falls outside this range, such as infants and the elderly.

In one embodiment, a therapeutically effective amount is the amount required to achieve at least an equivalent therapeutic effect compared to a standard therapy. An example of a standard therapy is an FDA-approved drug indicated for treating a particular disease or disorder. As a concrete example, Vascepa™ is an FDA-approved formulation of EPA, specifically an ethyl ester of EPA. Accordingly, in one aspect, the methods of the invention include administering to a subject a therapeutically effective amount of a compound of Formula IA or IB or a composition comprising same, or a composition comprising mixtures of at least two different compounds of Formula IA, as described herein, which is effective to reduce plasma triglycerides in an adult human subject by at least about 1 mmol/L, or by at least about 2 mmol/L.

In the context of any of the methods of the present invention, the subject may be a human or a non-human mammal. The non-human mammal may be, for example, a non-human primate, a dog, cat, a rodent (e.g., a mouse, a rat, a rabbit), a horse, a cow, a sheep, a goat, a bird, a chicken, or any other non-human mammal Preferably, the subject is a human.

In one embodiment, the subject is a human subject. In one embodiment, the human is an adult human, a pediatric human, or a geriatric human, as those terms are understood by the medical practitioner, for example as defined by the U.S. Food and Drug Administration.

The compositions of the invention can be used as monotherapy or adjunctive therapy. The compositions of the invention can be administered alone or in combination with one or more additional therapeutic agents (i.e., additional APIs) or therapies, for example as part of a therapeutic regimen that includes, e.g., aspects of diet and exercise. In certain embodiments, the methods of the invention include administration of a composition of the invention as the primary therapy. In other embodiments, the administration of a composition of the invention is an adjuvant therapy. In either case, the methods of the invention contemplate the administration of a composition of the invention in combination with one or more additional therapeutic agents and/or therapies for the treatment or prevention of a disease or disorder. The terms "therapy" and "therapies" refer to any method, protocol and/or agent that can be used in the prevention, treatment, management or amelioration of a disease or disorder, or one or more symptoms thereof.

Metabolic Disorders

In one embodiment, the invention provides methods of treating a metabolic disorder in a subject in need thereof, the method comprising administering to the subject, preferably a human subject, a composition comprising a compound of Formula IA or IB, or a mixture of compounds of Formula IA, a mixture of compounds of Formula IB, or mixtures of compounds of both Formula IA and IB.

In one embodiment, the method comprises administering a composition comprising a compound of Formula IA or a mixture of at least two different compounds of Formula IA wherein A and B are each a polyunsaturated fatty acid. In one embodiment, A and B are each independently selected from a fatty acid of the omega-3, omega-6, omega-7, or omega-9 series. In one embodiment, A and B are each omega-3 fatty acids independently selected from eicosapentaenoic acid (EPA), docosahexaenoic acid (DHA), and docosapentaenoic acid (DPA). In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA).

In one embodiment the metabolic disorder is selected from the group consisting of abnormal glucose metabolism manifesting in diabetes or pre-diabetes, abnormal lipid metabolism manifesting as hypertriglyceridemia, i.e., elevated triglycerides, mixed dyslipidemia, hypercholesterolemia, fatty liver, and combined abnormal glucose and lipid metabolism manifesting in obesity. In one embodiment the metabolic disorder is a dyslipidemic disorder selected from hypertriglyceridemia, hypercholesterolemia and mixed dyslipidemias. In one embodiment, the metabolic disorder is selected from the group consisting of pre-diabetes, type 2 diabetes, obesity, fatty liver disease, and insulin resistance.

In one embodiment, the methods comprise administering a therapeutically effective amount, which amount is effective to reduce plasma triglycerides in an adult human subject by at least about 0.5 mmol/L, about 1 mmol/L, or about 2 mmol/L.

In one embodiment, the subject is a human subject having severe hypertriglyceridemia characterized by serum triglyceride levels of from 500 to 2,000 mg/dl.

Cardiovascular Disorders

In one embodiment, the invention provides a method for treating cardiovascular disorders or complications relating to atrial fibrillation, myocardial infarction, and congestive heart failure by administering to a subject in need of such treatment an effective amount of a composition comprising a compound of Formula IA or IB, or a mixture of compounds of Formula IA, a mixture of compounds of Formula IB, or mixtures of compounds of both Formula IA and IB. In one embodiment, the method comprises administering a composition comprising a compound of Formula IA or a mixture of at least two different compounds of Formula IA wherein A and B are each a polyunsaturated fatty acid. In one embodiment, A and B are each independently selected from a fatty acid of the omega-3, omega-6, omega-7, or omega-9 series. In one embodiment, A and B are each omega-3 fatty acids independently selected from eicosapentaenoic acid (EPA), docosahexaenoic acid (DHA), and docosapentaenoic acid (DPA). In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the effective amount is effective to treat one or more symptoms of the cardiovascular condition.

Hematological Disorders

In one embodiment, the invention provides a method for treating hematological disorders or complications relating to sickle cell disease by administering to a subject in need of such treatment an effective amount of a composition comprising a compound of Formula IA or IB, or a mixture of compounds of Formula IA, a mixture of compounds of Formula IB, or mixtures of compounds of both Formula IA and IB. In one embodiment, the method comprises administering a composition comprising a compound of Formula IA or a mixture of at least two different compounds of Formula IA wherein A and B are each a polyunsaturated fatty acid. In one embodiment, A and B are each independently selected from a fatty acid of the omega-3, omega-6, omega-7, or omega-9 series. In one embodiment, A and B are each omega-3 fatty acids independently selected from eicosapentaenoic acid (EPA), docosahexaenoic acid (DHA), and docosapentaenoic acid (DPA). In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the effective amount is effective to treat one or more symptoms of the sickle cell disease.

Cancer Treatment and Prevention

In one embodiment, the invention provides a method for preventing cancer, the method comprising administering a therapeutically effective amount of a composition comprising a compound of Formula IA or IB, or a mixture of compounds of Formula IA, a mixture of compounds of Formula IB, or mixtures of compounds of both Formula IA and IB, to a subject in need of preventive anti-cancer therapy. In one embodiment, the method comprises administering a composition comprising a compound of Formula IA or a mixture of at least two different compounds of Formula IA wherein A and B are each a polyunsaturated fatty acid. In one embodiment, the cancer is colon cancer or familial adenomatous polyposis.

Inflammatory Disorders

The compounds of Formula IA and IB, and compositions comprising mixtures of the compounds of Formula IA, mixtures of the compounds of Formula IB, or a mixture of compounds of Formula IA, a mixture of compounds of Formula IB, or mixtures of compounds of both Formula IA and IB, may be particularly useful in the treatment of diseases and disorders having a significant inflammatory component, due to the anti-inflammatory properties of polyunsaturated fatty acids and the ability of the compounds of Formula IA and IB to deliver high amounts of free fatty acids to the serum by oral routes of administration.

In one embodiment, the invention provides a method for treating an inflammatory disorder, the method comprising administering to a subject in need of such treatment an effective amount of a composition comprising a compound of Formula IA or IB, or a mixture of compounds of Formula IA, a mixture of compounds of Formula IB, or mixtures of compounds of both Formula IA and IB. In one embodiment, A or B, or both are a polyunsaturated fatty acid. In one embodiment, A and B are each independently selected from a fatty acid of the omega-3, omega-6, omega-7, or omega-9 series. In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the effective amount is effective to treat one or more symptoms of the inflammatory disorder. In one embodiment, the inflammatory disorder is selected from the group consisting of arthritis, inflammatory bowel disease, and psoriasis.

In one embodiment, the invention provides methods of treating arthritis, irritable bowel syndrome, ophthalmic inflammation disorders, or dry eye syndrome in a subject in need of such treatment, the methods comprising administering to the subject a composition comprising a compound of Formula IA or IB, or a mixture of compounds of Formula IA, a mixture of compounds of Formula IB, or mixtures of compounds of both Formula IA and IB. In one embodiment, A or B, or both are a polyunsaturated fatty acid. In one embodiment, A and B are each independently selected from a fatty acid of the omega-3, omega-6, omega-7, or omega-9 series. In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA).

In one embodiment, the invention provides a method for treating a disease or disorder of the ocular system, also referred to as ophthalmic diseases and disorders, having an underlying inflammatory component, the method comprising administering to a subject in need of such treatment an effective amount of a composition comprising a compound of Formula IA or IB, or a mixture of compounds of Formula IA, a mixture of compounds of Formula IB, or mixtures of compounds of both Formula IA and IB. In one embodiment, A or B, or both are a polyunsaturated fatty acid. In one embodiment, A and B are each independently selected from a fatty acid of the omega-3, omega-6, omega-7, or omega-9 series. In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the effective amount is effective to treat one or more symptoms of the disease or disorder of the ocular system. In one embodiment, the disease or disorder of the ocular system is selected from the group consisting of inflammatory diseases of the eye, dry eye syndrome, macular edema and retinopathy. In one embodiment, the method is a method for promoting corneal wound healing.

In one embodiment, the invention provides a method for treating dry eye by administering a composition comprising a compound of Formula IA or IB, or a mixture of compounds of Formula IA, a mixture of compounds of Formula IB, or mixtures of compounds of both Formula IA and IB. In one embodiment, A or B, or both are a polyunsaturated fatty acid. In one embodiment, A and B are each independently selected from a fatty acid of the omega-3, omega-6, omega-7, or omega-9 series. In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). Dry eye disease or syndrome is a multifactorial disorder of the tears and ocular surface characterized by symptoms of dryness and irritation. Inflammation is an important component in the development and propagation of dry eye (Stevenson et al., *Arch. Ophthalmol.*, 2012, 130(1), 90-100; Rashid et al., *Arch. Ophthalmol.*, 2008, 126(2), 219-225).

The term 'dry eye' refers to inadequate tear production and/or abnormal tear composition. Causes of dry eye disease as defined herein include but are not limited to the following: idiopathic, congenital alacrima, xerophthalmia, lacrimal gland ablation, and sensory denervation; collagen vascular diseases, including rheumatoid arthritis, Wegener's granulomatosis, and systemic lupus erythematosus; Sjogren's syndrome and autoimmune diseases associated with Sjogren's syndrome; abnormalities of the lipid tear layer caused by blepharitis or rosacea; abnormalities of the mucin tear layer caused by vitamin A deficiency; trachoma, diphtheric keratoconjunctivitis; mucocutaneous disorders; aging; menopause; and diabetes. Further, the term "dry eye" includes dry eye after anterior ophthalmic operation such as cataract operation and refractive surgery and that accompanied with allergic conjunctivitis Dry eye symptoms as defined herein may also be provoked by other circumstances, including, but not limited to, the following: prolonged visual tasking; working on a computer; being in a dry environment; ocular irritation; contact lenses, LASIK and other refractive surgeries; fatigue; and medications such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine.

Neurological Disorders

In one embodiment, the invention provides a method for treating a psychiatric disorder in a subject, the method comprising administering the subject a therapeutically effective amount of a composition comprising a compound of Formula IA or IB, or a mixture of compounds of Formula IA, a mixture of compounds of Formula IB, or mixtures of compounds of both Formula IA and IB, where the amount is effective to treat one or more symptoms of the psychiatric disorder. In one embodiment, A or B, or both are a polyunsaturated fatty acid. In one embodiment, A and B are each independently selected from a fatty acid of the omega-3, omega-6, omega-7, or omega-9 series. In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the psychiatric disorder is selected from Alzheimer's disease, attention deficit hyperactivity disorder (ADHD) and depression.

In one embodiment, the invention provides a method for treating a neuro trauma injury in a subject, the method comprising administering to the subject a therapeutically effective amount of a composition comprising a compound of Formula IA or IB, or a mixture of compounds of Formula IA, a mixture of compounds of Formula IB, or mixtures of compounds of both Formula IA and IB, where the amount is effective to treat one or more symptoms of the neuro trauma injury. In one embodiment, A or B, or both are a polyunsaturated fatty acid. In one embodiment, A and B are each independently selected from a fatty acid of the omega-3, omega-6, omega-7, or omega-9 series. In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the neuro trauma injury is selected from traumatic brain injury, spinal cord injury, ischemic stroke, and concussion.

The invention also provides a method for treating epilepsy or epileptic syndrome by administering to a subject in need of such treatment a composition comprising a compound of Formula IB having one gabapentin molecule as the counter-ion component, or a compound of Formula IC having two gabapentin molecules as the counter-ion component. In one embodiment, the method comprises administering to the subject in need of treatment for epilepsy or epileptic syndrome a composition comprising a compound of Formula I, IA, IB, or IC, and at least one additional API. In one embodiment, the additional API is an anti-epileptic agent such as gabapentin, or a pharmaceutically acceptable salt and prodrug thereof.

Pain

The invention also provides a method for treating or managing pain. In one embodiment, the pain is neuropathic pain and the method comprises administering to a subject in need of treatment for neuropathic pain a pharmaceutical composition comprising a compound of Formula IA or a mixture of compounds of Formula IA and a non-steroidal anti-inflammatory agent (NSAID), or a pharmaceutically acceptable salt or prodrug thereof.

In one embodiment, the method comprises administering to a subject in need of treatment for neuropathic pain a pharmaceutical composition comprising a compound of Formula IB, or mixtures of 2 or more different Formula IB compounds, in which A or B is a polyunsaturated fatty acid, preferably EPA, DHA, or DPA, and the remainder is an NSAID.

In one embodiment, the pain is nociceptive pain and the method comprises administering to a subject in need of treatment for nociceptive pain a pharmaceutical composition comprising a compound of Formula IA or a mixture of compounds of Formula IA and gabapentin, or a pharmaceutically acceptable salt or prodrug thereof.

In one embodiment, the pain is nociceptive pain and the method comprises administering to a subject in need of treatment for nociceptive pain a pharmaceutical composition comprising a compound of Formula IB, or mixtures of 2 or more different Formula IB compounds, in which A or B is a polyunsaturated fatty acid, preferably EPA, DHA, or DPA, and the remainder is gabapentin, or a pharmaceutically acceptable salt or prodrug thereof.

Combination Therapies

In the context of combination therapies, a composition of the invention may be administered together with at least one additional API or separately from the additional API. Where delivery is together, a composition of the invention may be delivered in the same dosage form as the additional API, or in a different dosage form. One of the advantages of the present invention, as discussed above, is the ease of formulating the compositions described herein with additional APIs and excipients in a single solid dosage form due to their form as a free flowing powder that is chemically and physically stable (as opposed to the relatively unstable oily liquid form of free fatty acids and their esters).

In one embodiment, a composition of the invention is formulated in a single solid dosage form with an antihyperlipidemic agent or an anti-diabetic agent. Antihyperlipidemic agents that may be used include HMG CoA enzyme inhibitors (e.g., statins), cholesterol absorption inhibitors, and cholesterol esterase transfer protein (CETP) inhibitors. In one embodiment, the antihyperlipidemic agent is selected from a statin, a cholesterol absorption inhibitor, a CETP inhibitor, and pharmaceutically-acceptable salts and prodrugs of any of the foregoing. The pharmaceutically acceptable salt may be selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, and lactobionate salt.

In one embodiment, the antihyperlipidemic agent is a statin. In one embodiment, the statin is selected from the group consisting of atorvastatin, risuvostatin, simvastatin, pravastatin, and pharmaceutically acceptable salts and prodrugs of any of the foregoing. In one embodiment, the statin is present in an amount ranging from 5 mg to 100 mg. In one embodiment, the statin is pravastatin.

In one embodiment, the antihyperlipidemic agent is a cholesterol absorption inhibitor. In one embodiment, the cholesterol absorption inhibitor is ezetimibe, also known as Zetia.

In one embodiment, the antihyperlipidemic agent is a CETP inhibitor. In one embodiment, the CETP inhibitor is anacetrapib, or a hydrate, or solvate thereof.

In one embodiment, a composition of the invention is formulated in a single solid dosage form with an anti-epileptic agent or an inhibitor of neuropathic pain such as gabapentin, or a pharmaceutically acceptable salt and prodrug thereof.

The invention is further described in the following examples, which do not limit the scope of the invention described in the claims.

Non-Pharmaceutical Uses

In one embodiment, the invention provides compositions, particularly compositions of Formula IA and IB, in which A or B, or both, is a fatty acid, and mixtures of same, for a non-pharmaceutical use, e.g., for use as a dietary supplement or additive. In accordance with any of the embodiments described herein, the method may comprise administering to the subject an effective amount of a composition comprising a compound of Formula IA or IB, or a mixture of compounds of Formula IA, a mixture of compounds of Formula IB, or mixtures of compounds of both Formula IA and IB. In one embodiment, the method comprises administering a composition comprising a compound of Formula IA or a mixture of at least two different compounds of Formula IA wherein A and B are each a polyunsaturated fatty acid. In one embodiment, A and B are each independently selected from a fatty acid of the omega-3, omega-6, omega-7, or omega-9 series. In one embodiment, A and B are each omega-3 fatty acids independently selected from eicosapentaenoic acid (EPA), docosahexaenoic acid (DHA), and docosapentaenoic acid (DPA). In one embodiment, at least 50% of the fatty acid component of the composition consists of one or more omega-3 fatty acids independently selected from eicosapentaenoic acid (EPA), docosahexaenoic acid (DHA), and docosapentaenoic acid (DPA). In one embodiment, the effective amount is effective to maintain, promote, or improve the general health of the subject.

In one embodiment, the composition may be used in a method to counter a dietary deficiency or nutritional disorder in a subject. In one embodiment, the composition may be used in a method for maintaining, promoting, or improving the general health of a subject In one embodiment, the method is a method for improving prenatal health. In one embodiment of this method, the composition comprises from 50 mg to 6 g of DHA or total omega-3 fatty acids, and optionally further comprises one or more of a B vitamin, vitamin C, vitamin E, vitamin A, vitamin D, iron, zinc, calcium, iodine, metafolin, methylsulfonylmethane (also known as dimethyl sulfone and methyl sulfone), N-acetyl-L-cysteine, green tea extract (*Camellia sinensis*), and grape seed extract (*Vitis vinifera*). In one embodiment, the B vitamin is selected from thiamine (vitamin B-1), riboflavin (vitamin B-2), niacin (vitamin B-3), pantothenic acid (vitamin B-5), biotin (vitamin B-7), and folic acid (vitamin B-9), or any combination of the foregoing In one embodiment, the method is a method for improving heart health. In one embodiment of this method, the composition comprises from 50 mg to 6 g of EPA or total omega-3 fatty acids, and optionally further comprises one or more of coenzyme Q10, L-carnitine, an antioxidant, a phytosterol, and a flavonoid.

In one embodiment, the method is a method for improving joint health. In one embodiment of this method, the composition comprises from 50 mg to 6 g of EPA or total omega-3 fatty acids, and optionally further comprises one or more of chondroitin, glucosamine sulfate, calcium, vitamin D3, ginger extract, turmeric, curcumin, collagen, and a non-steroidal anti-inflammatory (NSAID).

In one embodiment, the method is a method for improving eye health. In one embodiment of this method, the composition comprises from 50 mg to 6 g of DHA or total omega-3 fatty acids, and optionally further comprises one or more of vitamin A, vitamin C, vitamin E, calcium, zinc, copper, selenium, a carotenoid, a flavonoid, and folic acid.

In one embodiment, the method is a method for improving cognitive health. In one embodiment of this method, the composition comprises from 50 mg to 6 g of EPA or total omega-3 fatty acids.

The invention is further described and exemplified by the following non-limiting examples.

EXAMPLES

Calcium Bis-Lysinate Monohydrate (Precursor)

A solution of L-lysine (14.62 g, 100 mmol) in water (HPLC grade, 100 mL) under nitrogen was treated with calcium hydroxide (2.67 g). After a few minutes the solid had mostly dissolved, and an additional 1.48 g of calcium hydroxide was added, bringing the total to 4.15 g (56 mmol). The aqueous mixture was stirred at room temperature for 3 h. The turbid solution was filtered through Celite, the filter cake rinsed with HPLC grade water, and the filtrate concentrated in vacuo to afford 16.50 g (86%) of subject material as a colorless foam. Calcd for $C_{12}H_{26}CaN_4O_4 \cdot H_2O$: C, 41.36; H, 8.10; N, 16.08. Found: C, 41.36; H, 7.95; N, 15.93. $^1H$ NMR ($D_2O$): δ 3.06 (t, 2H, J=7 Hz); 2.42 (t, 4H, J=7 Hz); 1.35-1.50 (m, 4H); 1.20-1.30 (m, 4H); 1.10-1.20 (m, 4H).

Calcium Bis-Lysinate Bis-EPA Monohydrate

A stirred solution of calcium bis-lysinate monohydrate (2.88 g, 7.5 mmol) in methanol (15 mL) was treated with a solution of EPA (4.84 g, 16 mmol) in methanol (15 mL) and stirred for 15 min, then diluted with acetonitrile (150 mL), stirred 30 min, and placed under refrigeration with cap for 24 h. The suspension was filtered and the waxy solid rinsed with acetonitrile and dried to afford 6.39 g (86%) of subject material as a pale orange solid. Calcd for $C_{52}H_{86}CaN_4O_8 \cdot H_2O$: C, 65.51; H, 9.30; N, 5.88. Found: C, 65.21; H, 9.06; N, 5.65. MP 138-141° C. $^1H$ NMR (d4-AcOH): δ 5.25-5.50 (m, 20H); 4.01 (t, 2H, J=6.5 Hz); 3.06 (t, 4H, J=6.5 Hz); 2.75-2.90 (m, 16H); 2.36 (t, 4H, J=6.5 Hz); 2.05-2.20 (m, 8H); 1.90-2.00 (m, 4H); 1.65-1.80 (m, 8H); 1.50-1.65 (m, 4H); 0.95 (t, 6H, J=6.5 Hz). $^{13}C$ NMR (d4-AcOH): δ 179.30, 174.08, 131.59, 128.71, 128.69, 128.24, 127.98, 127.97, 127.87, 127.68, 126.92, 54.33, 39.40, 32.87, 29.49, 26.18, 26.13, 25.22, 25.21, 25.11, 24.28, 21.37, 20.15, 13.48.

Calcium Bis-Lysinate Mono-EPA

A stirred solution of calcium bis-lysinate monohydrate (1.92 g, 5.0 mmol) in methanol (10 mL) was treated with a solution of EPA (1.55 g, 5.125 mmol) in methanol (10 mL) and stirred for 15 min, then concentrated in vacuo to a pale yellow foam. The above foam was triturated from acetonitrile (20 mL) and dried in vacuo to afford 3.26 g (97%) of subject material as a pale yellow powder. MP 141-143° C. $^1H$ NMR (d4-AcOH): δ 5.25-5.45 (m, 10H); 4.00 (t, 2H, J=6 Hz); 3.06 (t, 4H, J=7.5 Hz); 2.75-2.90 (m, 8H); 2.36 (t, 2H, J=7.5 Hz); 2.05-2.20 (m, 4H); 1.90-2.05 (m, 4H); 1.65-1.80 (m, 6H); 1.50-1.65 (m, 4H); 0.95 (t, 3H, J=7.5 Hz). $^{13}C$ NMR (d4-AcOH): δ 179.28, 174.14, 131.59, 128.71, 128.69, 128.24, 127.98, 127.96, 127.87, 127.68, 126.92, 54.34, 39.39, 32.88, 29.51, 26.20, 26.13, 25.22, 25.21, 25.11, 24.29, 21.39, 20.15, 13.48.

Calcium Bis-Lysinate Bis-DHA

A stirred solution of calcium bis-lysinate hydrate (1.533 g, 4.4 mmol) in methanol (15 mL) at 50° C. under nitrogen was treated with a solution of docosahexaenoic acid (DHA, 3.09 g, 9.4 mmol) in methanol (10 mL), allowed to cool to room temperature over 20 min, and partially concentrated in vacuo to remove most methanol. Acetonitrile (60 mL) was added, and the mixture stirred for 4 h, part of the time chilled. The pale yellow suspension was filtered and the amorphous solid rinsed with acetonitrile, collected and dried in vacuo to afford 4.26 g (98%) of subject material as a pale yellow solid. Calcd for $C_{56}H_{90}CaN_4O_8$: C, 68.12; H, 9.19; N, 5.67. Found: C, 68.06; H, 9.18; N, 5.06. MP 130-133° C. $^1H$ NMR (d4-AcOH): δ 5.25-5.45 (m, 24H); 4.01 (t, 2H, J=6.5 Hz); 3.06 (t, 4H, J=7.5 Hz); 2.75-2.95 (m, 20H); 2.30-2.45 (m, 8H); 2.05-2.15 (m, 4H); 1.90-2.05 (m, 4H); 1.70-1.80 (m, 4H); 1.50-1.65 (m, 4H); 0.95 (t, 6H, J=7.5 Hz). $^{13}C$ NMR (d4-AcOH): δ 178.75, 174.05, 131.59, 129.15, 128.23, 127.97, 127.95, 127.92, 127.89, 127.86, 127.68, 127.62, 126.93, 54.33, 39.39, 33.46, 29.47, 29.02, 28.46, 26.16, 25.24, 25.22, 25.18, 25.11, 22.22, 21.35, 20.15, 13.48.

Magnesium Bis-Lysinate Monohydrate

A stirred mixture of magnesium hydroxide (1.75 g, 30 mmol) and L-lysine (8.77 g, 60 mmol) in reagent ethanol (30 mL) under nitrogen was heated to reflux for 6 h and cooled to room temperature. The thick suspension was filtered (slow) and rinsed with ethanol, collected, and dried in vacuo to afford 9.86 g (89%) of subject compound as a white solid. $^1H$ NMR ($D_4$-AcOH): δ 4.00 (t, 2H, J=6 Hz); 3.06 (t, 4H, J=7.5 Hz); 1.90-2.05 (m, 4H); 1.71-1.78 (m, 4H); 1.52-1.63 (m, 4H). Elemental Analysis Calcd: C, 39.09; H, 8.75; N, 15.20. Found: C, 39.42; H, 8.47; N, 14.96. EA hits for trihydrate $C_{12}H_{26}MgN_4O_4 \cdot 3H_2O$.

Magnesium Bis-Lysinate Bis-EPA Dihydrate

A warmed (50° C.) stirred suspension of magnesium bis-lysinate monohydrate (1.844 g, 5.0 mmol) in methanol (10 mL) under nitrogen was treated with a solution of EPA (3.63 g, 12 mmol) in methanol (10 mL) containing alpha-D-tocopherol (100 mg) dissolved in ethyl acetate (0.5 mL), stirred for 20 min, then the mixture was concentrated in vacuo and suspended in acetonitrile (50 mL). The suspension was stirred for 3 h, filtered, washed with acetonitrile, collected and dried in vacuo to afford 4.78 g (100%) of magnesium lysinate bis EPA as a white solid. NMR ($d_4$-AcOH): δ 5.27-5.44 (m, 20H) 4.00 (t, 2H, J=6 Hz) 3.06 (t, 4H, J=7.5 Hz) 2.80-2.89 (m, 16H) 2.36 (t, 4H, J=7.5 Hz) 2.05-2.16 (m, 8H) 1.91-2.00 (m, 4H) 1.65-1.78 (m, 8H) 1.54-1.63 (m, 4H) 0.95 (t, 6H, J=7.5 Hz). Elemental Analysis from previous batch: Calcd: C, 65.36; H, 9.49; N, 5.86. Found: C, 65.12; H, 9.49; N. Passes as a dihydrate.

Magnesium Bis-Lysinate Mono-EPA

A warmed (50° C.) stirred suspension of magnesium bis-lysinate monohydrate (1.00 g, 3.0 mmol) in methanol (5 mL) under nitrogen was treated with a solution of EPA (0.94 g, 3.1 mmol) in methanol (10 mL) containing alpha-D-tocopherol (100 mg) dissolved in ethyl acetate (0.5 mL), and stirred for 20 min, then most of the methanol was removed in vacuo and replaced with acetonitrile (20 mL). The mixture was stirred for 3 h, filtered, washed with acetonitrile, collected and dried in vacuo to afford 1.855 g (100%) of subject material as a pale beige solid. MP 152-154° C. $^1H$ NMR (d4-AcOH): δ 5.25-5.45 (m, 10H); 3.99 (t, 2H, J=6 Hz); 3.06 (t, 4H, J=7.5 Hz); 2.75-2.90 (m, 8H); 2.36 (t, 2H, J=7.5 Hz); 2.05-2.20 (m, 4H); 1.90-2.05 (m, 4H); 1.65-1.80 (m, 6H); 1.50-1.65 (m, 4H); 0.95 (t, 3H, J=7.5 Hz). $^{13}C$ NMR (d4-AcOH): δ 179.27, 173.97, 131.60, 128.71, 128.24, 127.99, 127.97, 127.88, 127.68, 126.93, 54.35, 39.40, 32.90, 29.53, 26.21, 26.14, 25.23, 25.21, 25.12, 24.30, 21.41, 20.16, 13.50.

Magnesium Bis-Lysinate Bis-DHA Dihydrate

A warmed (50° C.) stirred suspension of magnesium bis-lysinate monohydrate (1.663 g, 5.0 mmol) in methanol (10 mL) under nitrogen was treated with a solution of DHA (3.53 g, 10.75 mmol) in methanol (10 mL) which had been combined with alpha-D-tocopherol (60 mg) in ethyl acetate (0.5 mL), and stirred for 20 min, then most of the methanol was removed in vacuo and replaced with acetonitrile (30 mL). The mixture was stirred for 3 h, filtered, washed with acetonitrile, collected and dried in vacuo to afford 4.85 g (96%) of subject material as a very pale beige solid. Calcd for $C_{56}H_{90}MgN_4O_8 \cdot 2H_2O$: C, 66.75; H, 9.40; N, 5.56. Found: C, 67.05; H, 9.49; N, 5.30. MP 147-150° C. $^1$H NMR (d4-AcOH): δ 5.25-5.45 (m, 24H); 4.01 (t, 2H, J=6 Hz); 3.07 (t, 4H, J=7.5 Hz); 2.75-2.95 (m, 20H); 2.35-2.45 (m, 8H); 2.05-2.15 (m, 4H); 1.90-2.05 (m, 4H); 1.70-1.80 (m, 4H); 1.50-1.65 (m, 4H); 0.95 (t, 6H, J=7.5 Hz). $^{13}$C NMR (d4-AcOH): δ 178.76; 173.91, 131.59, 129.15, 128.24, 127.97, 127.95, 127.89, 127.86, 127.68, 127.62, 126.93, 54.33, 39.40, 33.46, 29.46, 26.16, 25.24, 25.23, 25.22, 25.18, 25.11, 22.21, 21.34, 20.16, 13.48.

Magnesium Bis-Lysinate Mono-EPA Mono-DHA Dihydrate

A warmed (50° C.) stirred suspension of magnesium bis-lysinate trihydrate (1.844 g, 5.0 mmol) in methanol (25 mL) under nitrogen was treated with a solution of EPA (1.66 g, 5.5 mmol) and DHA (1.81, 5.5 mmol) in methanol (25 mL) which had been combined with alpha-D-tocopherol (100 mg) in ethyl acetate (1 mL), and stirred for 20 min, then the mixture was concentrated in vacuo and suspended in acetonitrile (75 mL). The mixture was stirred for 3 h, filtered, washed with acetonitrile, collected and dried in vacuo to afford 4.93 g (100%) of subject material as a pale beige solid. MP 153-155° C. $^1$H NMR (d4-AcOH): δ 5.25-5.45 (m, 22H); 4.00 (t, 2H, J=6 Hz); 3.07 (t, 4H, J=7.5 Hz); 2.80-2.90 (m, 18H); 2.40 (m, 4H); 2.37 (t, 2H, J=7.5 Hz); 2.10-2.17 (m, 2H); 2.08 (t, 4H, J=7.5 Hz); 1.92-2.02 (m, 4H); 1.72-1.80 (m, 4H); 1.65-1.70 (m, 2H); 1.52-1.62 (m, 4H); 0.96 (t, 6H, J=7.5 Hz). $^{13}$C NMR (d4-AcOH): δ 179.31, 178.75, 173.94, 131.59, 129.15, 128.71, 128.69, 128.24, 127.97, 127.95, 127.89, 127.87, 127.68, 127.63, 126.92, 54.33, 39.39, 33.47, 32.88, 29.48, 26.18, 26.13, 25.24, 25.22, 25.18, 25.11, 24.28, 22.22, 22.05, 21.36, 20.16, 13.49. LCMS (m-1): lysine (145.9, 100%); EPA (301.8, 100%); DHA (327.8, 100%).

Magnesium L-Lysinate Bis Stearic Acid

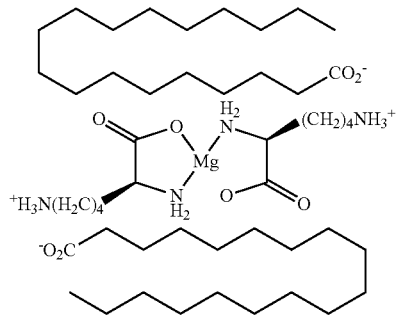

While under nitrogen, a suspension of magnesium lysinate (0.99 g, 2.66 mmol) in methanol (10 mL) was warmed to 50° C. and treated with a combined solution of stearic acid (1.83 g, 6.44 mmol) and alpha-D-tocopherol (50 mg pre-dissolved in 0.5 mL of ethyl acetate and added to the stearic acid solution) in methanol (10 mL). After stirring for 20 min, the mixture is cooled to room temperature and concentrated. The resulting foam is suspended in acetonitrile, stirred for 2 hours, collected by filtration, washed with acetonitrile and dried overnight in the vacuum oven to afford 2.49 g (99%) of Magnesium L-Lysinate bis stearic acid as a white solid. MP 168-171° C. $^1$H NMR (400 MHz, d4-AcOH): δ 4.04 (t, 2H, J=6.5 Hz) 3.08 (t, 4H, J=7.5 Hz) 2.35 (t, 4H, J=7.5 Hz) 2.03-1.97 (m, 4H) 1.77-1.72 (m, 4H) 1.64-1.55 (m, 8H) 1.32-1.29 (m, 56H) 0.88 (t, 6H, J=7.5 HZ).

Magnesium L-Lysinate Bis Linoleic Acid

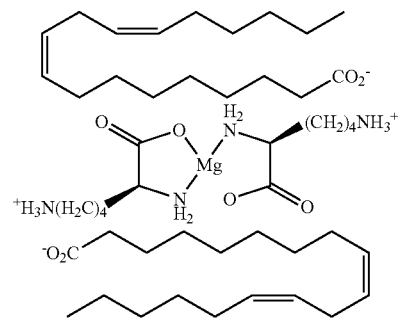

While under nitrogen, a suspension of magnesium lysinate (1.01 g, 2.74 mmol) in methanol (10 mL) was warmed to 50° C. and treated with a combined solution of linoleic acid (1.84 g, 6.57 mmol) and alpha-D-tocopherol (50 mg pre-dissolved in 0.5 mL of ethyl acetate and added to the linoleic acid solution) in methanol (10 mL). After stirring for 20 min, the mixture is cooled to room temperature and concentrated. The resulting foam is suspended in acetonitrile, stirred for 2 hours, collected by filtration, washed with acetonitrile and dried overnight in the vacuum oven to afford 2.50 g (98%) of Magnesium L-Lysinate bis linoleic acid as a white solid. MP 163-166° C. $^1$H NMR (400 MHz, d4-AcOH): δ 5.41-5.30 (m, 8H) 4.04 (t, 2H, J=6.5 Hz) 3.08 (t, 4H, J=7.5 Hz) 2.81-2.79 (m, 4H) 2.36 (t, 4H, J=7.5 Hz) 2.08-2.04 (m, 8H) 2.03-1.97 (m, 4H) 1.77-1.72 (m, 4H) 1.64-1.57 (m, 8H) 1.38-1.31 (m, 28H) 0.90 (t, 6H, J=7.5 Hz)

Magnesium L-Lysinate Bis Oleic Acid

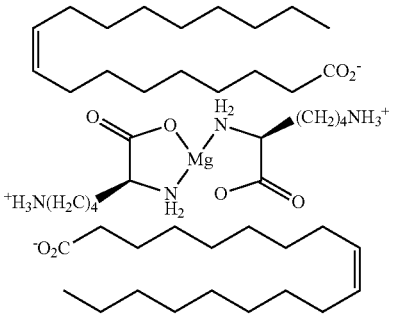

While under nitrogen, a suspension of magnesium lysinate (1.15 g, 3.12 mmol) in methanol (10 mL) was warmed to 50° C. and treated with a combined solution of oleic acid (2.11 g, 7.49 mmol) and alpha-D-tocopherol (50 mg pre-dissolved in 0.5 mL of ethyl acetate and added to the oleic acid solution) in methanol (10 mL). After stirring for 20 min, the mixture is cooled to room temperature and concentrated. The resulting foam is suspended in acetonitrile, stirred for 2 hours, collected by filtration, washed with acetonitrile and dried overnight in the vacuum oven to afford 2.87 g (99%) of Magnesium L-Lysinate bis oleic acid as a white solid. MP 165-168° C. ¹H NMR (400 MHz, d4-AcOH): δ 5.37-5.34 (m, 4H) 4.04 (t, 2H, J=6.5 Hz) 3.08 (t, 4H, J=7.5 Hz) 2.35 (t, 4H, J=7.5 Hz) 2.04-2.01 (m, 8H) 1.97-1.95 (m, 4H) 1.77-1.72 (m, 4H) 1.64-1.56 (m, 8H) 1.33-1.29 (m, 40H) 0.89 (t, 6H, J=7.5 Hz).

Magnesium L-Lysinate Bis Palmitic Acid

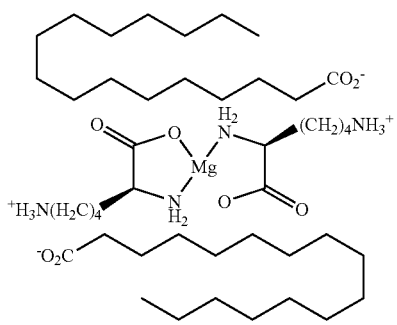

While under nitrogen, a suspension of magnesium lysinate (0.99 g, 2.66 mmol) in methanol (10 mL) was warmed to 50° C. and treated with a combined solution of palmitic acid (1.65 g, 6.44 mmol) and alpha-D-tocopherol (50 mg pre-dissolved in 0.5 mL of ethyl acetate and added to the palmitic acid solution) in methanol (10 mL). After stirring for 20 min, the mixture is cooled to room temperature and concentrated. The resulting foam is suspended in acetonitrile, stirred for 2 hours, collected by filtration, washed with acetonitrile and dried overnight in the vacuum oven to afford 2.33 g (98%) of Magnesium L-Lysinate bis palmitic acid as a white solid. MP 171-174° C. ¹H NMR (400 MHz, d4-AcOH): δ 4.04 (t, 2H, J=6.5 Hz) 3.07 (t, 4H, J=7.5 Hz) 2.35 (t, 4H, J=7.5 Hz) 1.99-1.96 (m, 4H) 1.77-1.73 (m, 4H) 1.64-1.60 (m, 8H) 1.34-1.29 (m, 48H) 0.88 (t, 6H, J=7.5 Hz).

Magnesium L-Lysinate Bis Linolenic Acid

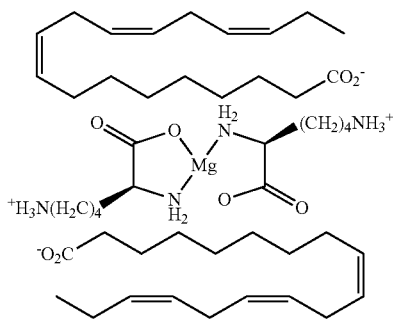

While under nitrogen, a suspension of magnesium lysinate (0.30 g, 0.81 mmol) in methanol (8 mL) was warmed to 50° C. and treated with a combined solution of linolenic acid (0.55 g, 1.95 mmol) and alpha-D-tocopherol (15 mg pre-dissolved in 0.3 mL of ethyl acetate and added to the linolenic acid solution) in methanol (7 mL). After stirring for 20 min, the mixture is cooled to room temperature and concentrated. The resulting foam is suspended in acetonitrile, stirred for 2 hours, collected by filtration, washed with acetonitrile and dried overnight in the vacuum oven to afford 0.71 g (94%) as a white solid. MP 166-169° C. ¹H NMR (400 MHz, d4-AcOH): δ 5.42-5.27 (m, 12H) 4.05 (t, 2H, J=6.5 Hz) 3.07 (t, 4H, J=7.5 Hz) 2.83-2.80 (m, 8H) 2.35 (t, 4H, J=7.5 Hz) 2.12-2.06 (m, 8H) 2.0-1.95 (m, 4H) 1.79-1.72 (m, 4H) 1.64-1.55 (m, 8H) 1.39-1.33 (m, 16H) 0.96 (t, 6H, J=7.5 Hz)

Magnesium Lysinate Bis Docosapentaenoic Acid

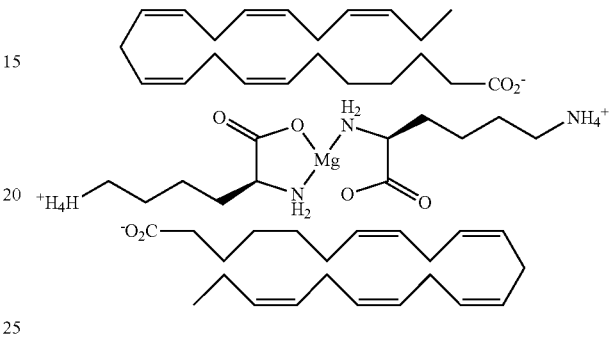

While under nitrogen, a suspension of magnesium lysinate (10.67 g, 28.9 mmol) in methanol (100 mL) was warmed to 50° C. and treated with docosapentaenoic acid (DPA) (22.0 g, 66.6 mmol) and alpha-D-tocopherol (600 mg pre-dissolved in 2 mL of ethyl acetate was added to the DPA solution) in methanol (100 mL). After stirring for 20 min, the mixture is cooled to room temperature and concentrated. The resulting foam is suspended in acetonitrile, stirred for 2 hours, collected by filtration, washed with acetonitrile and dried overnight in the vacuum oven to afford Magnesium L-Lysinate Bis-DPA (TP-452) 30.1 g, (101%) as a light tan solid. MP 154-157° C. ¹H NMR (400 MHz, d4-AcOH): δ 5.43-5.28 (m, 20H) 4.04 (t, 2H, J=6.5 Hz) 3.08 (t, 4H, J=7.5 Hz) 2.88-2.81 (m, 16H) 2.36 (t, 4H, J=7.5 Hz) 2.12-2.06 (m, 8H) 2.0-1.96 (m, 4H) 1.79-1.72 (m, 4H) 1.67-1.54 (m, 8H) 1.42-1.35 (m, 8H) 0.96 (t, 6H, J=7.5 Hz).

Zinc Bis-Lysinate

A stirred solution of zinc chloride (6.82 g, 50 mmol) in water (100 mL) was treated with potassium hydroxide (5.8 g, 103.4 mmol) in water (30 mL), and the precipitate was stirred at room temperature for 20 min (pH~9.5). The suspension was filtered, the solid washed with water three times, with ethanol three times, collected and dried under high vacuum and 60° C. for 6 h to afford 4.79 g (96%) of zinc hydroxide as a white solid. A stirred mixture of zinc hydroxide (4.48 g, 45 mmol) and L-lysine (13.45 g, 92 mmol) in ethanol (300 mL) was refluxed for 4 h (became very thick and required mechanical stirring). The above mixture was cooled to room temperature and filtered (slowly), collected, and dried in vacuo. The wet solid was triturated from acetonitrile and dried to afford 14.80 g (92%) of zinc bis-lysinate as a white powder. ¹H NMR (D₄-AcOH): δ 4.02 (m, 1H); 3.08 (m, 2H); 1.95-2.05 (m, 2H); 1.70-1.80 (m, 2H); 1.50-1.65 (m, 2H).

Zinc Bis-Lysinate Bis-EPA Monohydrate

A warmed (50° C.) stirred suspension of zinc bis-lysinate (1.78 g, 5.0 mmol) in methanol (15 mL) under nitrogen was treated with a solution of EPA (3.25 g, 10.75 mmol) in methanol (15 mL), at which point the solid dissolved. The solution was stirred for 20 min, then cooled to room temperature and concentrated in vacuo. The mixture was com bined with acetonitrile (70 mL), and the suspension was stirred for 3 h, then filtered and the solid rinsed with acetonitrile, collected, and dried in vacuo to afford 4.48 g (92%) of subject compound as a pale tan solid. Calcd for $C_{52}H_{86}ZnN_4O_8 \cdot H_2O$: C, 63.82; H, 9.06; N, 5.72. Found: C, 63.67; H, 9.01; N, 5.76. MP 95-98° C. $^1$H NMR (d4-AcOH): δ 5.25-5.45 (m, 20H); 4.03 (m, 2H); 3.08 (t, 4H, J=7.5 Hz); 2.80-2.90 (m, 16H); 2.36 (t, 4H, J=7.5 Hz); 2.05-2.20 (m, 8H); 1.95-2.05 (m, 4H); 1.65-1.80 (m, 8H); 1.55-1.65 (m, 4H); 0.95 (t, 6H, J=7.5 Hz).

TABLE 2

Examples of Compounds of Formula I and Formula IA (and certain precursors)

| Structure | Name | Characterization |
|---|---|---|
| 1 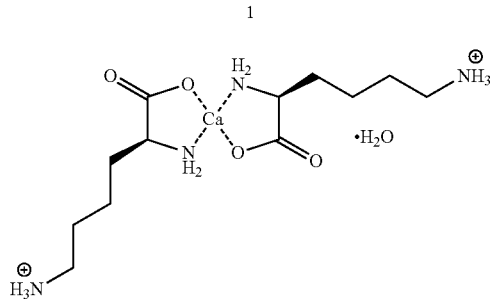 | Calcium bis-lysinate mono-hydrate (precursor) | Calcd for $C_{12}H_{26}CaN_4O_4 \cdot H_2O$: C, 41.36; H, 8.10; N, 16.08. Found: C, 41.36; H, 7.95; N, 15.93. $^1$H NMR (D$_2$O): δ 3.06 (t, 2H, J = 7 Hz); 2.42 (t, 4H, J = 7 Hz); 1.35-1.50 (m, 4H); 1.20-1.30 (m, 4H); 1.10-1.20 (m, 4H) |
| 2 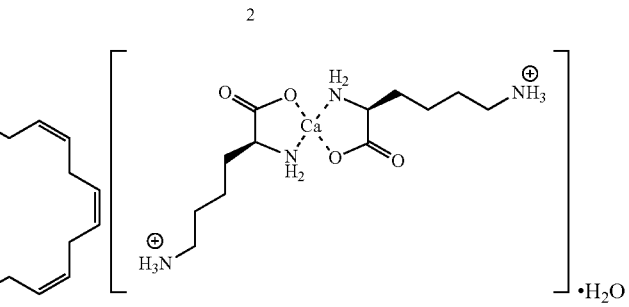 | Calcium bis-lysinate bis-EPA | Calcd for $C_{52}H_{86}CaN_4O_8 \cdot H_2O$: C, 65.51; H, 9.30; N, 5.88. 9.06; N, 5.65. MP 138-141° C. $^1$H NMR (d4-AcOH): δ 5.25-5.50 (m, 20H); 4.01 (t, 2H, J = 6.5 Hz); 3.06 (t, 4H, J = 6.5 Hz); 2.75-2.90 (m, 16H); 2.36 (t, 4H, J = 6.5 Hz); 2.05-2.20 (m, 8H); 1.90-2.00 (m, 4H); 1.65-1.80 (m, 8H); 1.50-1.65 (m, 4H); 0.95 (t, 6H, J = 6.5 Hz). $^{13}$C NMR (d4-AcOH): δ 179.30, 174.08, 131.59, 128.71, 128.69, 128.24, 127.98, 127.97, 127.87, 127.68, 126.92, 54.33, 39.40, 32.87, 29.49, 26.18, 26.13, 25.22, 25.21, 25.11, 24.28, 21.37, 20.15, 13.48 |
| 3 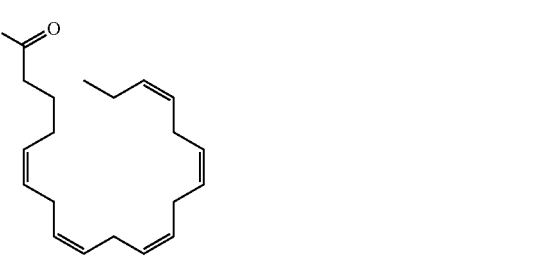 | Calcium bis-lysinate mono-EPA | MP 141-143° C. $^1$H NMR (d4-AcOH): δ 5.25-5.45 (m, 10H); 4.00 (t, 2H, J = 6 Hz); 3.06 (t, 4H, J = 7.5 Hz); 2.75-2.90 (m, 8H); 2.36 (t, 2H, J = 7.5 Hz); 2.05-2.20 (m, 4H); 1.90-2.05 (m, 4H); 1.65-1.80 (m, 6H); 1.50-1.65 (m, 4H); 0.95 (t, 3H, J = 7.5 Hz). $^{13}$C NMR (d4-AcOH): δ 179.28, 174.14, 131.59, 128.71, 128.69, 128.24, 127.98, 127.96, 127.87, 127.68, 126.92, 54.34, 39.39, 32.88, 29.51, 26.20, 26.13, 25.22, 25.21, 25.11, 24.29, 21.39, 20.15, 13.48 |

TABLE 2-continued

Examples of Compounds of Formula I and Formula IA (and certain precursors)

| Structure | Name | Characterization |
|---|---|---|
| 4 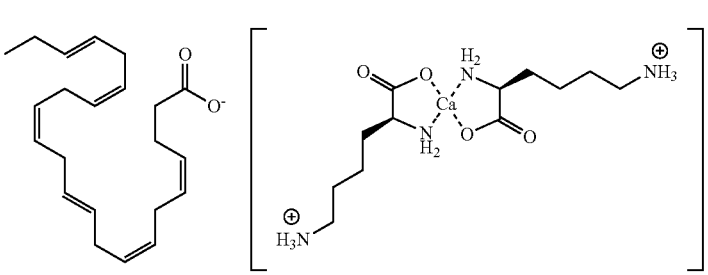 | Calcium bis-lysinate bis-DHA | Calcd for $C_{56}H_{90}CaN_4O_8$: C, 68.12; H, 9.19; N, 5.67. Found: C, 68.06; H, 9.18; N, 5.06. MP 130-133° C. $^1$H NMR (d4-AcOH): δ 5.25-5.45 (m, 24H); 4.01 (t, 2H, J = 6.5 Hz); 3.06 (t, 4H, J = 7.5 Hz); 2.75-2.95 (m, 20H); 2.30-2.45 (m, 8H); 2.05-2.15 (m, 4H); 1.90-2.05 (m, 4H); 1.70-1.80 (m, 4H); 1.50-1.65 (m, 4H); 0.95 (t, 6H, J = 7.5 Hz). $^{13}$C NMR (d4-AcOH): δ 178.75, 174.05, 131.59, 129.15, 128.23, 127.97, 127.95, 127.92, 127.89, 127.86, 127.68, 127.62, 126.93, 54.33, 39.39, 33.46, 29.47, 29.02, 28.46, 26.16, 25.24, 25.22, 25.18, 25.11, 22.22, 21.35, 20.15, 13.48 |
| 5 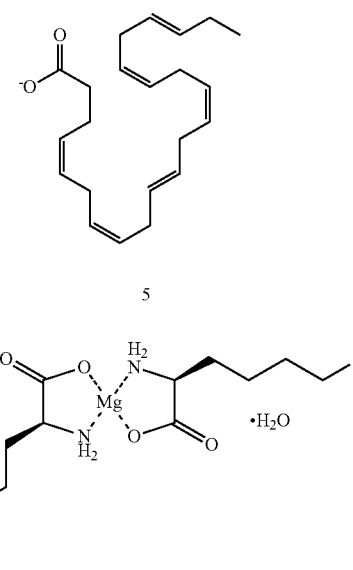 | Magnesium bis-lysinate monohydrate (precursor) | $^1$H NMR (D$_4$-AcOH): δ 4.00 (t, 2H, J = 6 Hz); 3.06 (t, 4H, J = 7 Hz); 1.90-2.05 (m, 4H); 1.70-1.80 (m, 4H); 1.50-1.65 (m, 4H) |
| 6 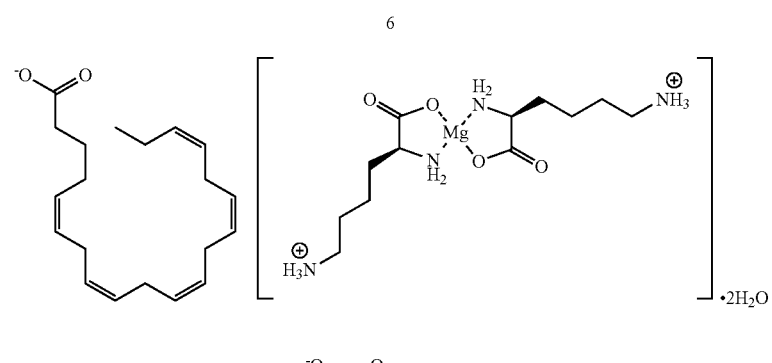 | Magnesium bis-lysinate bis-EPA Dihydrate | Calcd for $C_{52}H_{86}MgN_4O_8 \cdot 2H_2O$: C, 65.36; H, 9.49; N, 5.86. Found: C, 65.12; H, 9.49; N, 5.79. MP 153-155° C. $^1$H NMR (d4-AcOH): δ 5.25-5.45 (m, 20H); 4.01 (t, 2H, J = 6.5 Hz); 3.06 (t, 4H, J = 7.5 Hz); 2.80-2.90 (m, 16H); 2.37 (t, 4H, J = 7.5 Hz); 2.05-2.20 (m, 8H); 1.90-2.00 (m, 4H); 1.65-1.80 (m, 8H); 1.50-1.65 (m, 4H); 0.95 (t, 6H, J = 7.5 Hz). $^{13}$C NMR (d4-AcOH): δ 179.28, 173.98, 131.60, 128.71, 128.24, 127.99, 127.97, 127.88, 127.69, 126.93, 54.35, 39.40, 32.91, 29.53, 26.22, 26.15, 25.24, 25.22, 25.12, 24.30, 21.41, 20.17, 13.51 |

TABLE 2-continued

Examples of Compounds of Formula I and Formula IA (and certain precursors)

| Structure | Name | Characterization |
|---|---|---|
| 7 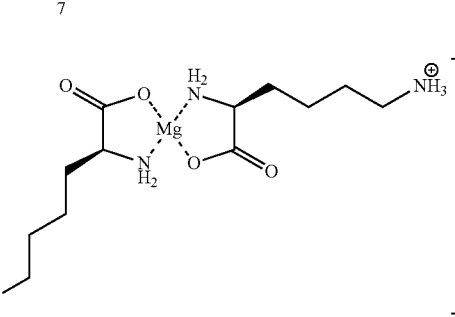 | Magnesium bis-lysinate mono-EPA | MP 152-154° C. $^1$H NMR (d4-AcOH): δ 5.25-5.45 (m, 10H); 3.99 (t, 2H, J = 6 Hz); 3.06 (t, 4H, J = 7.5 Hz); 2.75-2.90 (m, 8H); 2.36 (t, 2H, J = 7.5 Hz); 2.05-2.20 (m, 4H); 1.90-2.05 (m, 4H); 1.65-1.80 (m, 6H); 1.50-1.65 (m, 4H); 0.95 (t, 3H, J = 7.5 Hz). $^{13}$C NMR (d4-AcOH): δ 179.27, 173.97, 131.60, 128.71, 128.24, 127.99, 127.97, 127.88, 127.68, 126.93, 54.35, 39.40, 32.90, 29.53, 26.21, 26.14, 25.23, 25.21, 25.12, 24.30, 21.41, 20.16, 13.50 |
| 8 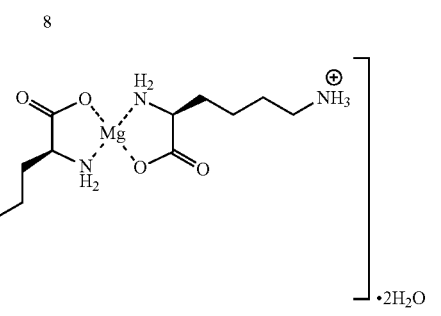 | Magnesium bis-lysinate bis-DHA Dihydrate | Calcd for $C_{56}H_{90}MgN_4O_8 \cdot 2H_2O$: C, 66.75; H, 9.40; N, 5.56. Found: C, 67.05; H, 9.49; N, 5.30. MP 147-150° C. $^1$H NMR (d4-AcOH): δ 5.25-5.45 (m, 24H); 4.01 (t, 2H, J = 6 Hz); 3.07 (t, 4H, J = 7.5 Hz); 2.75-2.95 (m, 20H); 2.35-2.45 (m, 8H); 2.05-2.15 (m, 4H); 1.90-2.05 (m, 4H); 1.70-1.80 (m, 4H); 1.50-1.65 (m, 4H); 0.95 (t, 6H, J = 7.5 Hz). $^{13}$C NMR (d4-AcOH): δ 178.76; 173.91, 131.59, 129.15, 128.24, 127.97, 127.95, 127.89, 127.86, 127.68, 127.62, 126.93, 54.33, 39.40, 33.46, 29.46, 26.16, 25.24, 25.23, 25.22, 25.18, 25.11, 22.21, 21.34, 20.16, 13.48 |
| 9 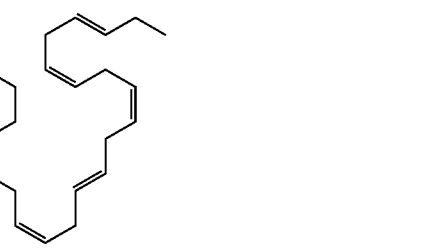 | Zinc bis-lysinate (precursor) | $^1$H NMR (D$_4$-AcOH): δ 4.02 (m, 1H); 3.08 (m, 2H); 1.95-2.05 (m, 2H); 1.70-1.80 (m, 2H); 1.50-1.65 (m, 2H) |

TABLE 2-continued

Examples of Compounds of Formula I and Formula IA (and certain precursors)

| Structure | Name | Characterization |
|---|---|---|
| 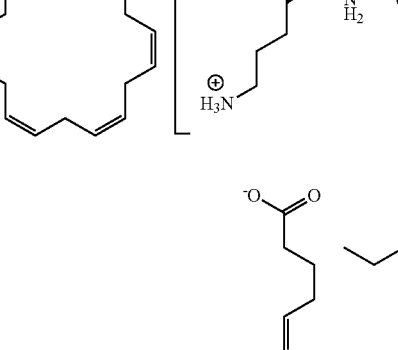 10 | Zinc bis-lysinate bis-EPA mono-hydrate | Calcd for $C_{52}H_{86}ZnN_4O_8 \cdot H_2O$: C, 63.82; H, 9.06; N, 5.72. Found: C, 63.67; H, 9.01; N, 5.76. MP 95-98° C. $^1$H NMR (d4-AcOH): δ 5.25-5.45 (m, 20H); 4.03 (m, 2H); 3.08 (t, 4H, J = 7.5 Hz); 2.80-2.90 (m, 16H); 2.36 (t, 4H, J = 7.5 Hz); 2.05-2.20 (m, 8H); 1.95-2.05 (m, 4H); 1.65-1.80 (m, 8H); 1.55-1.65 (m, 4H); 0.95 (t, 6H, J = 7.5 Hz) |
| 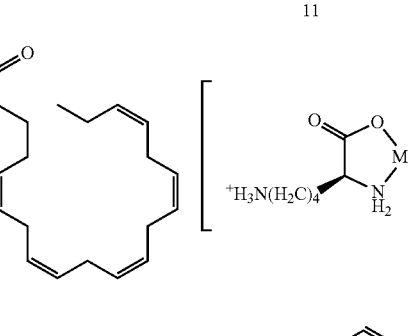 11 | Magnesium bis-lysinate mono-EPA mono-DHA dihydrate | $^1$H NMR (d4-AcOH): δ 5.25-5.45 (m, 22H); 4.00 (t, 2H, J = 6 Hz); 3.07 (t, 4H, J = 7.5 Hz); 2.80-2.90 (m, 18H); 2.40 (m, 4H); 2.37 (t, 2H, J = 7.5 Hz); 2.10-2.17 (m, 2H); 2.08 (t, 4H, J = 7.5 Hz); 1.92-2.02 (m, 4H); 1.72-1.80 (m, 4H); 1.65-1.70 (m, 2H); 1.52-1.62 (m, 4H); 0.96 (t, 6H, J = 7.5 Hz). $^{13}$C NMR (d4-AcOH): δ 179.31, 178.75, 1 73.94, 131.59, 129.15, 128.71, 128.69, 128.24, 127.97, 127.95, 127.89, 127.87, 127.68, 127.63, 126.92, 54.33, 39.39, 33.47, 32.88, 29.48, 26.18, 26.13, 25.24, 25.22, 25.18, 25.11, 24.28, 22.22, 22.05, 21.36, 20.16, 13.49. LCMS (m-1): lysine (145.9, 100%); EPA (301.8, 100%); DHA (327.8, 100%). |

Physical Stability Study

The compounds of the invention are remarkably stable compared to omega-3 polyunsaturated free fatty acids, which typically show evidence of oxidative degradation with hours of exposure to atmospheric oxygen. In contrast, as shown in FIG. 1, magnesium bis-lysinate bis-EPA was chemically stable for at least 60 days at room temperature exposed to air. The upper tracing in FIG. 1 is a proton NMR spectrum of magnesium bis-lysinate bis-EPA taken on the day the compound was synthesized. The lower tracing is the NMR taken 60-days later with the compound having been exposed to air at room temperature for the entire period. There is no evidence of oxidation or degradation by other mechanisms.

Bioavailability Study

The results of a single dose, oral pharmacokinetic study in rats for a compound of Formula III (designated TP-252, Mg-Lys$_2$-EPA$_2$) are shown in Table 3 below. One of the parameters shown in Table 1 is the area under the curve (AUC), which is the integral of a plot of concentration of drug in blood plasma against time. The AUC is proportional to the total amount of the active pharmaceutical agent (API) that reaches the blood circulation. In this example, the API (or analyte) is EPA. AUC and Cmax are given for the compound of Formula III, EPA free fatty acid (EPA FFA), and EPA ethyl ester (EPA EE). EPA ethyl ester is the FDA-approved form of EPA. These data demonstrate that TP-252 delivers significantly more EPA to the blood plasma than equivalent doses of either EPA free fatty acid or EPA ethyl ester.

TABLE 3

Baseline Adjusted, Molar Dose Equivalent
Total EPA Plasma Levels (ug/mL)

| Baseline and EPA Molar Dose Equivalent Adjusted | TP-252 | EPA EE | EPA FFA |
|---|---|---|---|
| $AUC_{0-18\ hrs}$ | 132.9 | 56.4 | 85.5 |
| $C_{max}$ | 13.2 | 6.8 | 7.6 |
| Total Dose (mg/kg) | 40.0 | 40.0 | 40.0 |
| EPA Molar Dose (mg/kg) | 26.3 | 36.6 | 39.2 |
| EPA Molar Dose Equivalent Adjustment Factor | 1.49 | 1.07 | 1.00 |
| Predose Total EPA Plasma Concentration (Hour = 0) | 3.1 | 3.9 | 4.6 | a) The Baseline Adjusted, Molar Dose Equivalent plasma levels of Total EPA shown in Table 1 are calculated based on Baseline Adjusted Total EPA Plasma Concentration levels, multiplied by the EPA Molar Dose Adjustment Factors.
b) Baseline Adjusted, EPA Molar Dose Equivalent Cmax means the unadjusted Total EPA Cmax level minus the Total EPA predose level, multiplied by the EPA Molar Dose Equivalent Adjustment Factors.
c) EPA Molar Dose (mg/kg) = Actual amount of EPA Free Fatty Acid delivered per kg of study subject.

Mixtures of Compounds of Formula Ia

Example 1: Magnesium Di-Arginate (Precursor)

A stirred mixture of powdered magnesium hydroxide (7.02 g, 120.3 mmol) and L-arginine (41.9 g, 240.6 mmol) in anhydrous ethanol (480 mL) under nitrogen was heated to reflux. After 30 minutes, water (120 mL) was added and the solution was heated again to reflux. After 5 hours the solution was cooled to 0° C. in an ice bath. The resulting suspension was filtered and rinsed with ethanol, and dried in vacuo to afford 41.5 g of magnesium arginate as a white solid (Note1). NMR ($d_4$-AcOH): δ 4.03 (t, 2H, J=6 Hz) 3.28 (t, 4H, J=7 Hz) 2.01-1.09 (m, 4H) 1.84-1.76 (m, 4H).

Example 2: Magnesium Di-Arginate Bis-5020FF

While under nitrogen, a suspension of magnesium arginate (0.75 g, 1.84 mmol) in methanol (10 mL) was warmed 50° C. with stirring. A combined solution of Kin Omega 5020FFA (1.42 g, 4.42 mmol, Note 2) and alpha-D-tocopherol (37 mg, Note 3, pre-dissolved in 0.5 mL of ethyl acetate and added to the 5020FFA solution) in methanol (10 mL) was added. After 20 minutes, the suspension was cooled to room temperature and concentrated. The resulting foam was suspended in acetonitrile (30 mL) with stirring for 2 hours, collected by vacuum filtration, washed with acetonitrile and dried in a vacuum oven to give magnesium arginate bis-5020FF (1.86 g) as an off-white solid. MP 90-93° C. NMR ($d_4$-AcOH): δ 5.44-5.28 (m) 4.04 (t) 3.28 (t) 2.89-2.87 (m) 2.42-2.34 (m) 2.17-1.99 (m) 1.85-1.77 (m) 1.74-1.61 (m) 1.40-1.29 (m) 0.96 (t) 0.91-0.87 (m).

Example 3: Magnesium Di-Arginate Bis F1070

While under nitrogen, a suspension of magnesium arginate (1.17 g, 2.88 mmol) in methanol (15 mL) was warmed 50° C. A combined solution of Croda Incromega F1070 (2.21 g, 6.90 mmol, Note 2) and alpha-D-tocopherol (58 mg, pre-dissolved in 0.5 mL of ethyl acetate and added to the F1070 solution) in methanol (15 mL) was added. After 20 minutes the suspension was cooled to room temperature and concentrated. The resulting foam was suspended in acetonitrile (30 mL) with stirring for 2 hours, collected by vacuum filtration, washed with acetonitrile and dried in a vacuum oven to afford magnesium arginate bis-F1070 (2.92 g) as an off-white solid. MP 96-99° C. NMR ($d_4$-AcOH): δ 5.46-5.28 (m) 4.04 (t) 3.28 (t) 2.91-2.86 (m) 2.42-2.34 (m) 2.18-1.99 (m) 1.85-1.78 (m) 1.74-1.61 (m) 1.40-1.29 (m) 0.96 (t) 0.91-0.87 (m).

Example 4: Magnesium Di-Arginate Bis F7010

While under nitrogen, a suspension of magnesium arginate (1.0 g, 2.46 mmol) in methanol (12 mL) was warmed to 50° C. A combined solution of Croda Incromega F7010 (1.88 g, 5.90 mmol, Note 2) and alpha-D-tocopherol (50 mg, pre-dissolved in 0.5 mL of ethyl acetate and added to the F7010 solution) in methanol (12 mL) was added. After 20 minutes the suspension was cooled to room temperature and concentrated. The resulting foam was suspended in acetonitrile (30 mL) with stirring for 2 hours, collected by vacuum filtration, washed with acetonitrile and dried in a vacuum oven to give magnesium arginate bis-F7010 (2.32 g) as an off-white solid. MP 98-101° C. NMR ($d_4$-AcOH): δ 5.45-5.28 (m) 4.04 (t) 3.28 (t) 2.91-2.83 (m) 2.42-2.34 (m) 2.17-1.99 (m) 1.85-1.77 (m) 1.74-1.61 (m) 1.44-1.29 (m) 0.96 (t) 0.91-0.87 (m).

Example 5: Magnesium Di-Arginate Bis F4030

While under nitrogen, a suspension of magnesium arginate (1.0 g, 2.46 mmol) in methanol (12 mL) was warmed to 50° C. A combined solution of Croda Incromega F4030 (1.88 g, 5.90 mmol) and alpha-D-tocopherol (50 mg, Note 3, pre-dissolved in 0.5 mL of ethyl acetate and added to the F4030 solution) in methanol (12 mL) was added. After 20 minutes the suspension was cooled to room temperature and concentrated. The resulting foam was suspended in acetonitrile (30 mL) with stirring for 2 hours, collected by vacuum filtration, washed with acetonitrile and dried in a vacuum oven to afford magnesium arginate bis-F4030 (2.28 g) as an off-white solid. MP 109-112° C. NMR ($d_4$-AcOH): δ 5.46-5.30 (m) 4.04 (t) 3.28 (t) 2.91-2.86 (m) 2.42-2.34 (m) 2.17-1.99 (m) 1.85-1.77 (m) 1.74-1.61 (m) 1.44-1.29 (m) 0.96 (t) 0.91-0.87 (m).

Example 6: Magnesium Lysinate Bis-550200

Magnesium lysinate (0.98 g, 2.66 mmol) was weighed into a 100 mL pear shaped flask. Methanol (10 mL) was added and the suspension stirred under nitrogen at 50° C. A combined solution of KD Pharma 550200FFAA4 (2.05 g, 6.39 mmol, Note 2) and alpha-D-tocopherol (54 mg, Note 3, pre-dissolved in 0.5 mL of ethyl acetate and added to the 550200 FFA solution) in methanol (10 mL) was added. After 20 minutes the suspension was cooled to room temperature, the solvent removed in vacuo and the foam suspended in acetonitrile. The suspension stirred for 2 hours, was collected by vacuum filtration, washed with acetonitrile and dried in a vacuum oven to afford 2.59 g of Magnesium lysinate bis 550200 as an off-white solid. MP 150-153 NMR ($d_4$-AcOH): δ 5.44-5.28 (m) 4.04 (t) 3.08 (t) 2.89-2.87 (m) 2.42-2-2.34 (m) 2.17-1.94 (m) 1.80-1.56 (m) 1.38-1.29 (m) 0.96 (t) 0.89-0.86 (m).

Example 7: Magnesium Lysinate Bis-5520

Magnesium lysinate (0.95 g, 2.58 mmol) was weighed into a 100 mL pear shaped flask. Methanol (10 mL) was added and the suspension stirred under nitrogen at 50° C. A combined solution of KinOmega 5520FFA (1.98 g, 6.18 mmol, Note 2) and alpha-D-tocopherol (52 mg, Note 3, pre-dissolved in 0.5 mL of ethyl acetate and added to the 5520 FFA solution) in methanol (10 mL) was added. After 20 minutes the suspension was cooled to room temperature, the solvent removed in vacuo and the foam suspended in acetonitrile. The suspension stirred for 2 hours, was collected by vacuum filtration, washed with acetonitrile and dried in a vacuum oven to afford 2.61 g of Magnesium lysinate bis 5520 as an off-white solid. MP 151-154° C. NMR (d$_4$-AcOH): δ 5.45-5.28 (m) 4.04 (t) 3.07 (t) 2.89-2.85 (m) 2.41-2-2.35 (m) 2.17-1.94 (m) 1.81-1.53 (m) 1.38-1.29 (m) 0.96 (t) 0.89-0.86 (m).

Example 8: Comparison of Amounts of Fatty Acids Present in the Starting Blend Croda Incromega F4030 and Product Blend Magnesium Di-Arginate Bis F4030

Evaporative light scattering detection (ELSD) was used to measure the relative amounts of the two main fatty acids, EPA and DHA, present in a commercially available free fatty acid blend (Croda Incromega F4030) as well as the amounts of these two fatty acids in a composition of the invention prepared according to the methods described herein from the same commercial blend. In this example, the composition produced was a magnesium di-Arginate bis-fatty acid, prepared according to the process described in Example 5. The ELSD system was coupled to a high liquid chromatography (HPLC) system for separation of the individual components. Flow rate was 0.5 ml/min, solvent system used a gradient of 50-100% acetonitrile in water using 0.1% trifluoroacetic (TFA) acid as a mobile phase modifier.

The results of this analysis were as follows. The ratio of EPA:DHA in the starting blend was 1.4:1. The ratio of EPA:DHA in the resulting composition was also 1.4:1. Similarly, additional testing with synthetic blends of pure EPA and DHA demonstrated that the ratio of these fatty acids in a composition prepared according to the process described in Example 5 remained about the same as was present in the starting blend. These results are summarized in the table below.

| % EPA in blend | % DHA in blend | ratio EPA:DHA in blend | ratio EPA:DHA final composition |
|---|---|---|---|
| 47 | 53 | 0.9:1 | 0.9:1 |
| 85 | 15 | 5.7:1 | 5.5:1 |
| 10 | 90 | 0.1:1 | 0.1:1 |

These results demonstrate that the proportional amount of particular fatty acids to each other (such as EPA to DHA) present in the counter-ion component of the composition is essentially the same as in the starting blend of free fatty acids. Thus, a composition of the invention can be prepared having any desired ratio of fatty acids in relation to each other simply by making (or obtaining) a starting blend of free fatty acids having the fatty acids in the desired ratio to each other.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A compound of Formula I which is a mono or bis salt of a polyunsaturated fatty acid having an amino acid component, which consists of two amino acid moieties coordinated around a divalent metal cation, a metal component, which consists of a divalent metal cation, and a counter-ion component, which consists of one or two additional molecules, A and B, ionically bound to the amino acid component,

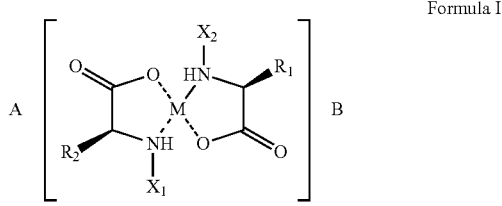

Formula I wherein
R$_1$ and R$_2$ each refer to a branched or unbranched carbon chain of from 1 to 20 carbons having at least one basic function;
R$_1$ and R$_2$ are the same or different and the at least one basic function is independently selected from a primary amine, a secondary amine, a tertiary amine, and a guanidine;
X$_1$ and X$_2$ are independently selected from H and —CO—Z, where Z is a peptide moiety incorporating from 1 to 5 amino acids, or a pharmaceutically acceptable salt thereof;
X$_1$ and X$_2$ are the same or different;
M is a divalent metal cation selected from magnesium (Mg$^{2+}$), calcium (Ca$^{2+}$), and zinc (Zn$^{2+}$);
A and B are each independently selected from a polyunsaturated fatty acid having 16 to 24 carbon atoms
either A or B, but not both, may be absent, and
when both A and B are present, A and B may be the same or different.

2. The compound of claim 1, wherein X$_1$ and X$_2$ are each H.

3. The compound of claim 2, wherein R$_1$ and R$_2$ are each (CH$_2$)$_3$—Y$_1$ and Y$_1$ is NHC(NH$_2$+)NH$_2$.

4. The compound of claim 2, wherein R$_1$ and R$_2$ are each (CH$_2$)$_4$—Y$_2$ and Y$_2$ is NH$_3$+.

5. The compound of claim 4, wherein each polyunsaturated fatty acid is independently selected from an omega-3 fatty acid, an omega-6 fatty acid, an omega-7 fatty acid, and an omega-9 fatty acid.

6. The compound of claim 5, wherein A and B are independently selected from eicosapentaenoic acid (EPA), docosahexaenoic acid (DHA), and docosapentaenoic acid (DPA), hexadecatrienoic acid (HTA), α-Linolenic acid (ALA), stearidonic acid (SDA), eicosenoic acid, eicosatrienoic acid (ETE), all-cis-5,8,11-eicosatrienoic acid, eicosatetraenoic acid (ETA), heneicosapentaenoic acid (HPA), tetracosapentaenoic acid, tetracosahexaenoic acid, linoleic acid, gamma-linolenic acid (GLA), calendic acid, eicosadienoic acid, dihomo-gamma-linolenic acid (DGLA), arachidonic acid, adrenic acid, docosadienoic acid, docosapentaenoic acid (Osbond acid), tetracosapentaenoic acid, 24:5 (n-6), tetracosatetraenoic acid, palmitoleic acid, vaccenic acid, paullinic acid, oleic acid, elaidic acid, gondoic acid, mead acid, erucic acid, and nervonic acid.

7. The compound of claim 6, wherein the polyunsaturated fatty acid is an omega-3 fatty acid selected from the group consisting of eicosapentaenoic acid (EPA), docosahexaenoic acid (DHA), docosapentaenoic acid (DPA), hexadecatrienoic acid (HTA), α-linolenic acid (ALA), stearidonic acid (SDA), eicosatrienoic acid (ETE), eicosatetraenoic acid (ETA), heneicosapentaenoic acid (HPA), tetracosapentaenoic acid, and tetracosahexaenoic acid.

8. The compound of claim 7, wherein the omega-3 fatty acid is selected from eicosapentaenoic acid (EPA), docosahexaenoic acid (DHA), and docosapentaenoic acid (DPA).

9. The compound of claim 6, wherein the polyunsaturated fatty acid is an omega-6 fatty acid selected from the group consisting of linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (Osbond acid), tetracosatetraenoic acid, and tetracosapentaenoic acid, 24:5 (n-6).

10. The compound of claim 6, wherein the polyunsaturated fatty acid is an omega-9 fatty acid selected from the group consisting of mead acid, 20:3 (n-9), all-cis-5,8,11-eicosatrienoic acid, oleic acid, eicosenoic acid, erucic acid, and nervonic acid.

11. A dosage form comprising the compound of claim 1 and an optional carrier, the dosage form selected from a gel, a cream, a powder, a tablet, a capsule, a caplet, or an aqueous solution.

12. A pharmaceutical composition comprising the compound of claim 1 and a pharmaceutically acceptable carrier.

13. The pharmaceutical composition of claim 12, wherein the composition further comprises one or more additional active pharmaceutical agents (APIs).

14. The pharmaceutical composition of claim 13, wherein the one or more additional APIs is selected from the group consisting of antihyperlipidemic agent, an anti-diabetic agent, an anti-epileptic agent, and an anti-inflammatory agent, and combinations thereof.

15. The pharmaceutical composition of claim 14, wherein the one or more additional APIs is an antihyperlipidemic agent is selected from an HMG CoA enzyme inhibitor, a cholesterol absorption inhibitor, and a cholesterol esterase transfer protein (CETP) inhibitor, and combinations thereof.

16. The pharmaceutical composition of claim 15, wherein the antihyperlipidemic agent is a statin.

17. The pharmaceutical composition of claim 16, wherein the statin is selected from the group consisting of atorvastatin, risuvostatin, simvastatin, pravastatin, and pharmaceutically acceptable salts or prodrugs thereof.

18. A solid unit dosage form comprising the compound claim 1.

19. The solid unit dosage form of claim 18, wherein the unit dosage form comprises from about 0.05 g to 12 g of total fatty acids.

20. A method for delivering free fatty acids, or a mixture of two or more different free fatty acids, in ionic form to a subject, the method comprising administering to the subject the compound of claim 1.

21. A method for delivering free fatty acids, or a mixture of free fatty acids, in ionic form and at least one divalent metal cation selected from magnesium ($Mg^{2+}$), calcium ($Ca^{2+}$), and zinc ($Zn^{2+}$) to a subject, the method comprising administering to the subject the compound of claim 1.

22. A method for treating a disease or disorder responsive to treatment with a polyunsaturated fatty acid, the method comprising administering to the subject the compound of claim 1.

23. The method of claim 22, wherein at least 50 wt % of the fatty acid component of the compound or composition consists of one or more omega-3 fatty acids independently selected from eicosapentaenoic acid (EPA), docosahexaenoic acid (DHA), and docosapentaenoic acid (DPA).

24. The method of claim 22, wherein the disease or disorder is selected from a metabolic disease or disorder, a cardiovascular disease or disorder, a hematological disorder, cancer, an inflammatory disease or disorder, and a neurological disease or disorder.

25. The method of claim 24, wherein the metabolic disease or disorder is type 2 diabetes, pre-diabetes, insulin resistance, hypertriglyceridemia due to elevated triglycerides, mixed dyslipidemia, hypercholesterolemia, fatty liver or obesity due to the combination of abnormal glucose and lipid metabolism.

26. The method of claim 24, wherein the metabolic disease or disorder is hypertriglyceridemia, severe hypertriglyceridemia, hypercholesterolemia, pre-diabetes, fatty liver disease, or obesity.

27. The method of claim 24, wherein the cardiovascular disease or disorder is atrial fibrillation, myocardial infarction, or congestive heart failure.

28. The method of claim 24, wherein the cancer is familial adenomatous polyposis.

29. The method of claim 24, wherein the inflammatory disease or disorder is arthritis, inflammatory bowel disease, or psoriasis.

30. The method of claim 24, wherein the inflammatory disease or disorder is an ophthalmic inflammation disorder or dry eye syndrome.

31. The method of claim 24, wherein the neurological disease or disorder is a psychiatric disorder selected from Alzheimer's disease, attention deficit hyperactivity disorder (ADHD) or depression.

32. The method of claim 24, wherein the neurological disease or disorder is a neuro trauma injury selected from traumatic brain injury, spinal cord injury, ischemic stroke, or concussion.

33. The compound of claim 1, wherein $R_1$ and $R_2$ are each $(CH_2)_4$—$NH_3^+$, $X_1$ and $X_2$ are each H, and A and B are both present and the same and are selected from eicosapentaenoic acid (EPA), docosahexaenoic acid (DHA), docosapentaenoic acid (DPA) and arachidonic acid (AA).

34. The compound of claim 33, wherein the divalent metal cation is $Mg^{2+}$.

35. The compound of claim 33, wherein the divalent metal cation is $Ca^{2+}$ or $Zn^{2+}$.

36. The compound of claim 34, wherein A and B are AA.

37. The compound of claim 35, wherein A and B are EPA.

38. The compound of claim 35, wherein A and B are DHA.

39. The compound of claim 35, wherein A and B are DPA.

40. The compound of claim 35, wherein A and B are AA.

41. A compound of Formula I which is a bis salt of a polyunsaturated fatty acid having an amino acid component, which consists of two amino acid moieties coordinated around a divalent metal cation, a metal component, which consists of a divalent metal cation, and a counter-ion component, which consists of one or two additional molecules, A and B, ionically bound to the amino acid component,

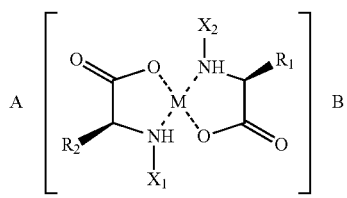

Formula I wherein
$R_1$ and $R_2$ are each $(CH_2)_4—NH_3^+$;
$X_1$ and $X_2$ are each H;
M is magnesium ($Mg^{2+}$); and
A and B are each eicosapentaenoic acid (EPA).

42. A dosage form comprising the compound of claim 41 and an optional carrier, the dosage form selected from a gel, a cream, a powder, a tablet, a capsule, a caplet, or an aqueous solution.

43. A pharmaceutical composition comprising the compound of claim 41 and a pharmaceutically acceptable carrier.

44. The pharmaceutical composition of claim 43, wherein the composition further comprises one or more additional active pharmaceutical agents (APIs).

45. The pharmaceutical composition of claim 44, wherein the one or more additional APIs is selected from the group consisting of antihyperlipidemic agent, an anti-diabetic agent, an anti-epileptic agent, and an anti-inflammatory agent, and combinations thereof.

46. The pharmaceutical composition of claim 45, wherein the one or more additional APIs is an antihyperlipidemic agent selected from an HMG CoA enzyme inhibitor, a cholesterol absorption inhibitor, and a cholesterol esterase transfer protein (CETP) inhibitor, and combinations thereof.

47. The pharmaceutical composition of claim 46, wherein the antihyperlipidemic agent is a statin.

48. The pharmaceutical composition of claim 47, wherein the statin is selected from the group consisting of atorvastatin, risuvostatin, simvastatin, pravastatin, and pharmaceutically acceptable salts or prodrugs thereof.

49. A solid unit dosage form comprising the compound of claim 41.

50. The solid unit dosage form of claim 49, wherein the unit dosage form comprises from about 0.05 g to 12 g of total fatty acids.

51. A method for treating a metabolic disease or disorder in a human subject in need thereof, the method comprising administering to the subject a pharmaceutical composition comprising an effective amount of the compound of claim 41, wherein the metabolic disease or disorder is selected from, type 2 diabetes, pre-diabetes, insulin resistance hypertriglyceridemia due to elevated triglycerides, mixed dyslipidemia, hypercholesterolemia, fatty liver or obesity due to the combination of abnormal glucose and lipid metabolism.

52. The method of claim 51, wherein the metabolic disease or disorder is selected from hypertriglyceridemia, severe hypertriglyceridemia, hypercholesterolemia, pre-diabetes, fatty liver disease, and obesity.

53. A method for treating an inflammatory disease or disorder in a human subject in need thereof, the method comprising administering to the subject a pharmaceutical composition comprising an effective amount of the compound of claim 41, wherein the inflammatory disease or disorder is arthritis or psoriasis.

54. A method for treating inflammatory bowel disease in a human subject in need thereof, the method comprising administering to the subject a pharmaceutical composition comprising an effective amount of the compound of claim 41.

55. A method for treating familial adenomatous polyposis in a human subject in need thereof, the method comprising administering to the subject a pharmaceutical composition comprising an effective amount of the compound of claim 41.

56. A compound of Formula I which is a bis salt of a polyunsaturated fatty acid having an amino acid component, which consists of two amino acid moieties coordinated around a divalent metal cation, a metal component, which consists of a divalent metal cation, and a counter-ion component, which consists of one or two additional molecules, A and B, ionically bound to the amino acid component,

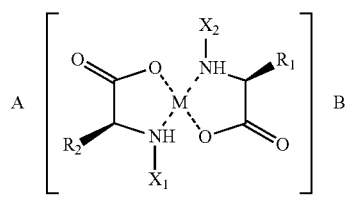

Formula I wherein
$R_1$ and $R_2$ are each $(CH_2)_4—NH_3^+$;
$X_1$ and $X_2$ are each H;
M is magnesium ($Mg^{2+}$); and
A and B are each docosahexaenoic acid (DHA).

57. A compound of Formula I which is a bis salt of a polyunsaturated fatty acid having an amino acid component, which consists of two amino acid moieties coordinated around a divalent metal cation, a metal component, which consists of a divalent metal cation, and a counter-ion component, which consists of one or two additional molecules, A and B, ionically bound to the amino acid component,

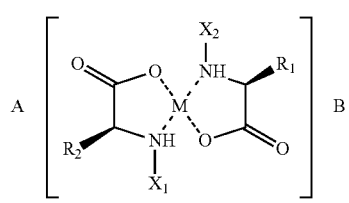

Formula I wherein
$R_1$ and $R_2$ are each $(CH_2)_4—NH_3^+$;
$X_1$ and $X_2$ are each H;
M is magnesium ($Mg^{2+}$); and
A and B are each docosapentaenoic acid (DPA).

* * * * *